US008222383B2

(12) United States Patent
Yamanashi et al.

(10) Patent No.: US 8,222,383 B2
(45) Date of Patent: Jul. 17, 2012

(54) DNA ENCODING POLYPEPTIDE CAPABLE OF MODULATING MUSCLE-SPECIFIC TYROSINE KINASE ACTIVITY

(75) Inventors: Yuji Yamanashi, Tokyo (JP); Osamu Higuchi, Tokyo (JP); Kumiko Okada, Tokyo (JP); Akane Inoue, Tokyo (JP)

(73) Assignee: National University Corporation, Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 12/329,208

(22) Filed: Dec. 5, 2008

(65) Prior Publication Data

US 2009/0158448 A1 Jun. 18, 2009

Related U.S. Application Data

(63) Continuation of application No. PCT/JP2007/059050, filed on Apr. 26, 2007.

(30) Foreign Application Priority Data

Jun. 7, 2006 (JP) .................................. 2006-158987

(51) Int. Cl.
C07H 21/04 (2006.01)
C07H 21/02 (2006.01)
C12Q 1/37 (2006.01)
(52) U.S. Cl. ...................... 536/23.2; 536/23.1; 435/325
(58) Field of Classification Search .................. 536/23.1
See application file for complete search history.

(56) References Cited

U.S. PATENT DOCUMENTS 7,157,566 B2 * 1/2007 Tsien et al. .................. 536/23.1

FOREIGN PATENT DOCUMENTS

| EP | 1 308 459 A2 | 5/2003 |
| EP | 1580263 | 9/2005 |
| JP | H11-29599 | 2/1999 |
| WO | 2005/014813 | 2/2005 |

OTHER PUBLICATIONS

Chiu TL et al.,Optimizing energy potentials for success in protein tertiary structure prediction, Folding and Design, 1998, 3:223-228.*
Wallace et al., Methods Enzymol, vol. 152, pp. 432-443, 1987.*
Sambrook et al., Molecular Cloning, 2nd Edition, 1989, Cold Spring Harbor Laboratory, Cold Spring Harbor, NY, p. 11.47.*
Kennell, DE, 1971, Progr Nucl. Acid Res. Mol. Biol., 11:259-301.*
GenBank Acc. No.AB0220918, Higuchi, O., The muscle protein Dok-7 is essential for neuromuscular synaptiogenesis, Jun. 4, 2006, US National Library of Medicine, Bethesda, MD, accessed by PTO on Jul. 8, 2009.*
Sequence alignmentGenBank Acc. No.AB0220918 and pending SEQ ID No. 1.*
Zhu et al, PNAS, 2003, 200:2231-2236).*

Andrew G. Engel et al., "Sleuthing Molecular Targets for Neurological Diseases at the Neuromuscular Junction", Nature Reviews Neuroscience, vol. 4, May 2003, pp. 339-352.
Angela Vincent et al., "Antibodies in Myasthenia Gravis and Related Disorders", Annals New York Academy of Sciences, vol. 998, 2003, pp. 324-335.
David J. Glass et al., "Agrin Acts via a MuSK Receptor Complex", Cell, vol. 85, May 17, 1996, pp. 513-523.
Steven J. Burden, "The formation of neuromuscular synapses", Genes & Development, vol. 12, 1998, pp. 133-148.
Joshua R. Sanes et al., "Induction, Assembly, Maturation and Maintenance of a Postsynaptic Apparatus", Nature Reviews Neuroscience, vol. 2, Nov. 2001, pp. 791-805.
Thomas M. DeChiara et al., "The Receptor Tyrosine Kinase MuSK is Required for Neuromuscular Junction Formation In Vivo", Cell, vol. 85, May 17, 1996, pp. 501-512.
Weichun Lin et al., "Distinct roles of nerve and muscle in postsynaptic differentiation of the neuromuscular synapse", Nature, vol. 410, Apr. 26, 2001, pp. 1057-1064.
Xia Yang et al., "Patterning of Muscle Acetylcholine Receptor Gene Expression in the Absence of Motor Innervation", Neuron, vol. 30, May 2001, pp. 399-410.
Thomas Misgeld et al., "Agrin promotes synaptic differentiation by counteracting an inhibitory effect of neurotransmitter", PNAS, vol. 102, No. 31, Aug. 2, 2005, pp. 11088-11093.
Weichun Lin et al., "Neurotransmitter Acetylcholine Negatively Regulates Neuromuscular Synapse Formation by a Cdk5-Dependent Mechanism", Neuron, vol. 46, May 19, 2005, pp. 569-579.
Andrew G. Engel et al., "Current understanding of congenital myasthenic syndromes", Current Opinion in Pharmacology, vol. 5, 2005, pp. 308-321.
Feng Cong et al., "Characterization of a Novel Member of the DOK Family That Binds and Modulates Abl Signaling", Molecular and Cellular Biology, Dec. 1999, pp. 8314-8325.
Jan Grimm et al., "Novel p62dok family members, dok-4 and dok-5, are substrates of the c-Ret receptor tyrosine kinase and mediate neuronal differentiation", The Journal of Cell Biology, vol. 154, No. 2, Jul. 23, 2001, pp. 345-354.
Robert J. Crowder et al., "Dok-6, a Novel p62 Dok Family Member, Promotes Ret-mediated Neurite Outgrowth", The Journal of Biological Chemistry, vol. 279, No. 40, Oct. 1, 2004, pp. 42072-42081.
Heather Zhou et al., "Distinct Domains of MuSK Mediate Its Abilities to Induce and to Associate with Postsynaptic Specializations", The Journal of Cell Biology, vol. 146, No. 5, Sep. 6, 1999, pp. 1133-1146.
Ruth Herbst et al., "The juxtamembrane region of MuSK has a critical role in agrin-mediated signaling", The EMBO Journal, vol. 19, No. 1, 2000, pp. 67-77.
Ruth Herbst et al., "Restoration of synapse formation in Musk mutant mice expressing a Musk/Trk chimeric receptor", Development 129, 2002, pp. 5449-5460.

(Continued)

*Primary Examiner* — Valerie Bertoglio
(74) *Attorney, Agent, or Firm* — Hoffmann & Baron, LLP

(57) ABSTRACT

Disclosed are DNA encoding a polypeptide which can modulate the activity of a muscle-specific tyrosine kinase, and others. The DNA is selected from the following members (a) to (d): (a) DNA comprising a specific nucleotide sequence; (b) DNA comprising a nucleotide sequence capable of hybridizing with a specific nucleotide sequence under stringent conditions; (c) DNA comprising a nucleotide sequence encoding an amino acid sequence having the substitution, deletion and/or addition of one or several amino acid residues in a specific amino acid sequence; and (d) DNA comprising a nucleotide sequence having 90% or higher homology to a specific nucleotide sequence.

4 Claims, 22 Drawing Sheets

OTHER PUBLICATIONS

Terrance T. Kummer et al., "Nerve-independent formation of a topologically complex postsynaptic apparatus", The Journal of Cell Biology, vol. 164, No. 7, Mar. 29, 2004, pp. 1077-1087.

Andreas Sander et al., "MuSK induces in vivo acetylcholine receptor clusters in a ligand-independent manner", The Journal of Cell Biology, vol. 155, No. 7, Dec. 24, 2001, pp. 1287-1296.

Christian Fuhrer et al., "Association of muscle-specific kinase MuSK with the acetylcholine receptor in mammalian muscle", The EMBO Journal, vol. 16, No. 16, 1997, pp. 4951-4960.

Frederic Chevessier et al., "MUSK, a new target for mutations causing congenital myasthenic syndrome", Human Molecular Genetics, vol. 13, No. 24, 2004, pp. 3229-3240.

"Accession: BC089590 [gi: 58476251], Definition: Mus musculus Riken cDNA A930013K19 gene, mRNA (cDNA clone MGC:107606 Image:6759981), complete cds", NCBI Sequence Revision History [online]; Sep. 9, 2005 updated, NCBI, <URL: http://www.ncbi.nlm.nih.gov/entrez/viewer.fcgi?58476251:NCBI:11253721> [Retrieved on Jun. 13, 2007], Retrieved from the Internet: <URL: http://www.ncbi.nlm.nih.gov/entrez/sutils/girevhist.cgi? val=BC089590>.

The extended European search report issued to European Application No. 07742485.1, mailed Aug. 27, 2009.

Office Action for EP 07 742 485.1-2401 dated Nov. 17, 2010.

\* cited by examiner

FIG. 3
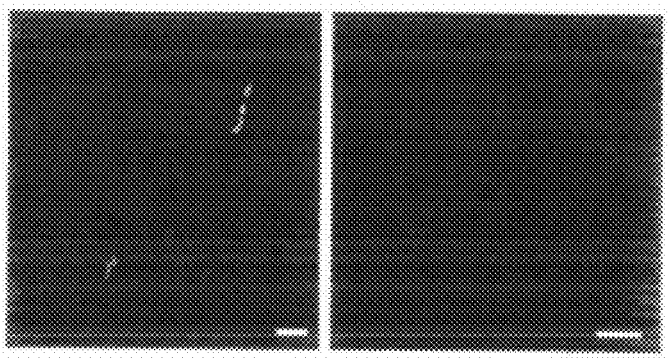
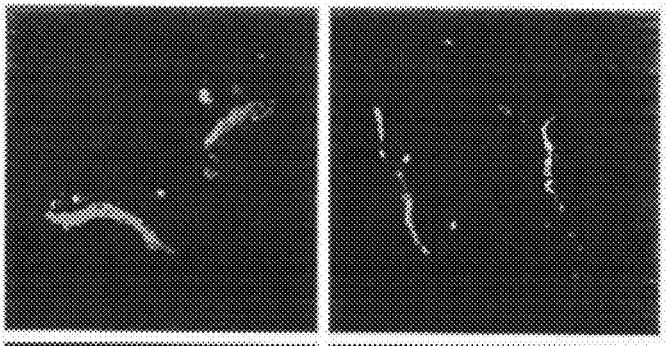
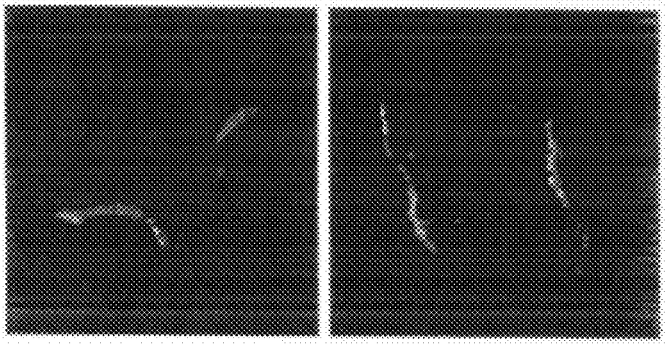

FIG. 11
ANTISENSE
SENSE

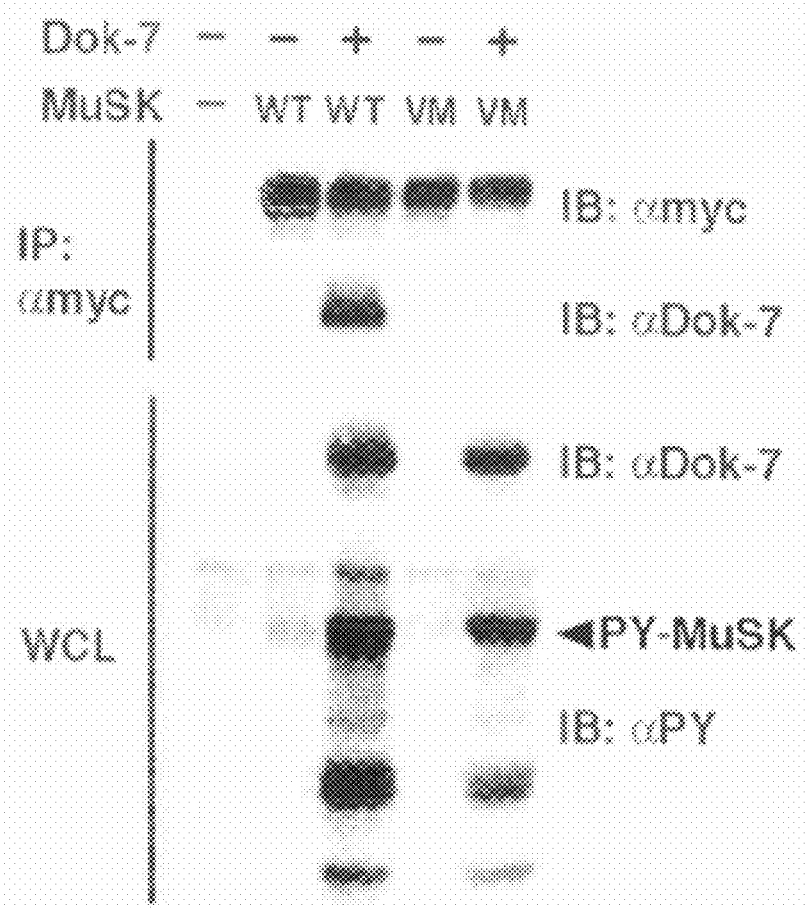

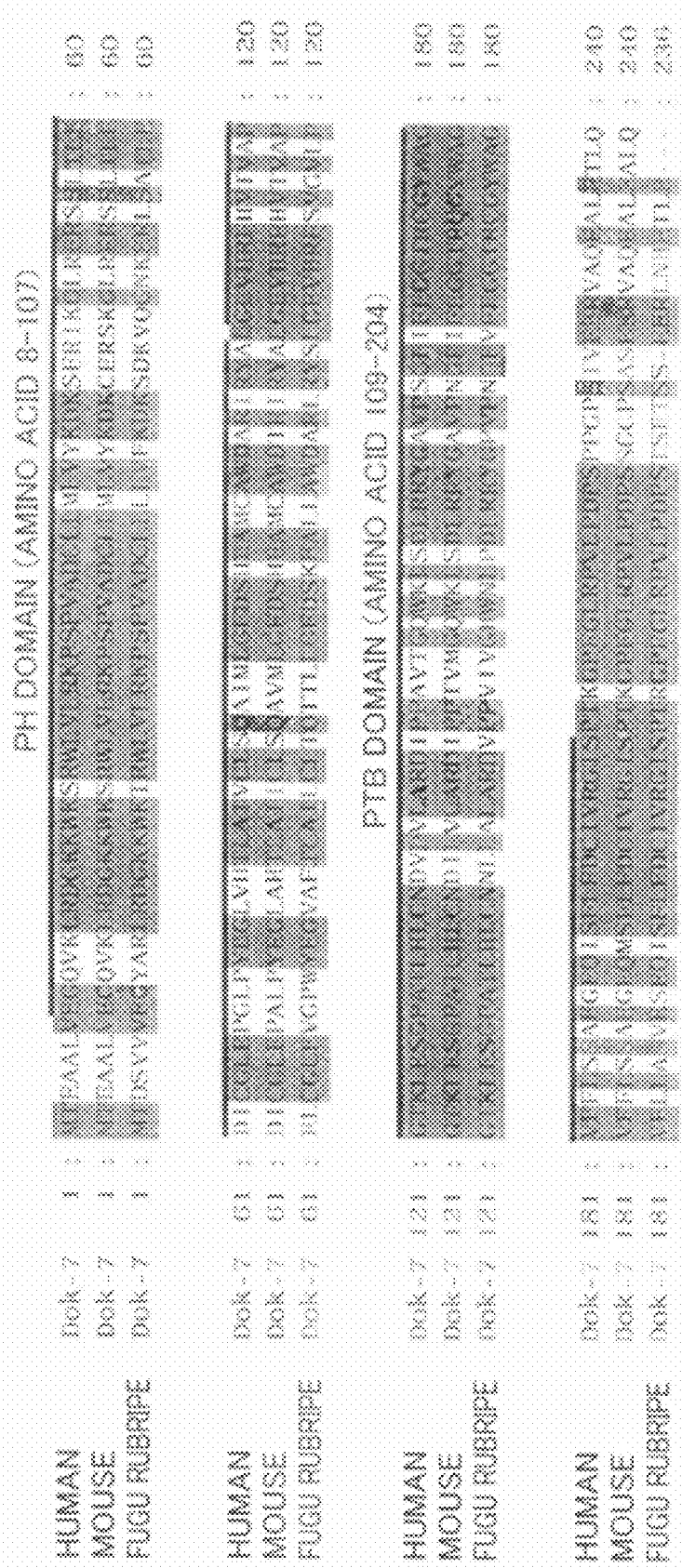

DNA ENCODING POLYPEPTIDE CAPABLE OF MODULATING MUSCLE-SPECIFIC TYROSINE KINASE ACTIVITY

CROSS-REFERENCE TO RELATED APPLICATIONS

This application is a continuation of International Application No. PCT/JP2007/059050, filed Apr. 26, 2007, which claims priority to Japanese Patent Application No. 2006-158987, filed Jun. 7, 2006, the contents of each of which are incorporated herein by reference.

TECHNICAL FIELD

The present invention relates to: a DNA encoding a polypeptide which modulates the activity of a muscle-specific tyrosine kinase; a vector including the DNA; a transformant having the vector introduced therein; a polypeptide encoded by the DNA; an antibody that binds to the polypeptide; a nonhuman transformed animal in which the DNA is deficient or mutated; a pharmaceutical composition including the DNA and/or the polypeptide; a test method and a test agent for a disease derived from an abnormality in the neuromuscular junction (for example, congenital myasthenic syndrome); a screening method for a compound candidate for a therapeutic drug for a disease derived from an abnormality in the neuromuscular junction; and the like.

BACKGROUND ART

Neuromuscular junction (hereinafter, may be also referred to as "NMJ") constructed with a motor nerve terminal joined with a muscle is an essential synapse in controlling skeletal muscle by the motor nerve via the neurotransmitter acetylcholine. For appropriately controlling the skeletal muscle, it is necessary to form a high-density site (hereinafter, may be also referred to as "cluster") through clustering of acetylcholine receptors (hereinafter, may be also referred to as "AChR") in a postsynaptic region of a neuromuscular junction. It has been revealed that neuromuscular transmission disorders such as congenital myasthenic syndrome and myasthenia gravis may be developed when a high-density site of acetylcholine receptors is not normally formed (see, Nonpatent Documents 1 and 2).

It was reported that a glycoprotein, i.e., agrin, is secreted by motor nerve endings to activate MuSK that is a muscle-specific tyrosine kinase (see, Nonpatent Document 3). In addition, activation of MuSK that occurs in an agrin-dependent manner was reported to be essential in forming and maintaining the postsynaptic structure including a high-density site of acetylcholine receptors (see, Nonpatent Documents 4 and 5).

However, it was found that even before the muscle is controlled by the nerve, the high-AChR density site is formed in the vicinity of the endplate of the myotube in a manner independent to nerve and agrin, and in a manner dependent to MuSK. This finding suggests that the high-AChR density site is formed by a mechanism derived from the muscle in the initial stage of development (see, Nonpatent Documents 6 to 8).

Furthermore, agrin-independent formation of NMJ was found in mice in which a neurotransmission-dependent inhibitory action on clustering of AChR was eliminated by loss of acetylcholine productivity. This finding suggests that an activating factor of MuSK may be present in addition to agrin (see, Nonpatent Documents 9 and 10).

Moreover, as a result of genetic research, it was also indicated that not only appropriate growth of axon, but also normal expression of AChR gene, and clustering of AChR that subsequently occurs are controlled by a MuSK-dependent mechanism derived from the muscle (see, Nonpatent Documents 7 and 8).

Accordingly, clustering of AChR is essential for preventing neuromuscular transmission disorders, and it has been proven that the MuSK activation is prerequisite for clustering of AChR.

Nonpatent Document 1: A. G. Engel, K. Ohno and S. M. Sine, "Nature Reviews Neuroscience", 4, 339 (2003)

Nonpatent Document 2: A. Vincent et al., "Annals of the New York Academy of Sciences", 998, 324 (2003)

Nonpatent Document 3: D. J. Glass et al., "Cell", 85, 513 (1996)

Nonpatent Document 4: S. J. Burden, "Genes and Development", 12, 133 (1998)

Nonpatent Document 5: J. R. Sanes and J. W. Lichtman, "Nature Reviews Neuroscience", 2, 791 (2001)

Nonpatent Document 6: T. M. DeChiara et al., "Cell", 85, 501 (1996)

Nonpatent Document 7: W. Lin et al., "Nature", 410, 1057 (2001)

Nonpatent Document 8: X. Yang et al., "Neuron", 30, 399 (2001)

Nonpatent Document 9: T. Misgeld et al., "Proceedings of the National Academy of Sciences, U.S.A", 102, 11088 (2005)

Nonpatent Document 10: W. Lin et al., "Neuron", 46, 569 (2005)

DISCLOSURE OF THE INVENTION

Problems to be Solved by the Invention

However, the mechanism activated by MuSK is almost entirely unclear. Therefore, it is strongly desired to clarify the mechanism by which MuSK is activated, and to enable modulation of the activity of MuSK.

An object of the present invention is to provide: a DNA encoding a polypeptide which can modulate the activity of MuSK; a vector including the DNA; a transformant having the vector introduced therein; a polypeptide encoded by the DNA; an antibody that binds to the polypeptide; a nonhuman transformed animal in which the DNA is deficient or mutated; a pharmaceutical composition including the DNA and/or the polypeptide; a test method and a test agent for a disease derived from an abnormality in the neuromuscular junction (for example, congenital myasthenic syndrome); a screening method for a compound candidate for a therapeutic drug for a disease derived from an abnormality in the neuromuscular junction; and the like.

Means for Solving the Problems

The present inventors found a novel polypeptide (hereinafter, may be also referred to as "Dok-7 protein") belonging to Dok family protein (a kind of intracellular signal transduction proteins) which modulates a variety of cellular activities (growth, survival, migration, differentiation, and the like). Furthermore, it was found that the Dok-7 protein is expressed in muscular tissues at high levels, and participates in MuSK activation. Accordingly, the present invention was completed.

Specifically, the present invention provides the following.

In a first aspect, provided is a DNA encoding a polypeptide that modulates the activity of a muscle-specific tyrosine kinase, the DNA being selected from the following members (a) to (d):

(a) a DNA including the nucleotide sequence set out in SEQ ID NO: 2;

(b) a DNA including a nucleotide sequence capable of hybridizing with the nucleotide sequence set out in SEQ ID NO: 2 under stringent conditions;

(c) a DNA including a nucleotide sequence encoding an amino acid sequence having the substitution, deletion and/or addition of one or several amino acid residues in the amino acid sequence set out in SEQ ID NO: 1; and (d) a DNA including a nucleotide sequence having 90% or higher homology to the nucleotide sequence set out in SEQ ID NO: 2.

In a second aspect, provided is a vector including the DNA according to the first aspect.

In a third aspect, provided is a transformant in which the vector according to the second aspect is introduced.

In a fourth aspect, provided is a polypeptide encoded by the DNA according to the first aspect.

In a fifth aspect, provided is a method for producing the polypeptide according to the fourth aspect, the method including: culturing the transformant according to the third aspect; and recovering the synthesized polypeptide from the transformant or culture fluid.

In a sixth aspect, provided is an antibody or an antibody fragment that binds to the polypeptide according to the fourth aspect.

In a seventh aspect, provided is a nonhuman transformed animal in which a DNA including the nucleotide sequence set out in SEQ ID NO: 2, or at least a part of the DNA of the expression control region thereof is deficient or mutated.

In an eighth aspect, provided is a pharmaceutical composition including the DNA according to the first aspect or the polypeptide according to the fourth aspect, as an active ingredient.

In a ninth aspect, provided is a test method for a disease derived from an abnormality in a neuromuscular junction, including the steps of:

extracting a DNA from a cell of a subject;

amplifying the extracted DNA as a template by performing a polymerase chain reaction using a primer capable of specifically amplifying a DNA including the nucleotide sequence set out in SEQ ID NO: 2, or a part or all of the DNA of the expression control region thereof;

reading the nucleotide sequence of the amplified DNA; and comparing the read nucleotide sequence with the nucleotide sequence set out in SEQ ID NO: 2.

In a tenth aspect, provided is a test method for a disease derived from an abnormality in a neuromuscular junction, including the steps of:

determining the amount of expression of a DNA having the nucleotide sequence set out in SEQ ID NO: 2 in a cell of a subject; and comparing the determined amount of expression of the DNA with the amount of expression of the DNA set out in SEQ ID NO: 2 in a cell of healthy individual.

In an eleventh aspect, provided is a test agent for a disease derived from an abnormality in the neuromuscular junction, including as an active ingredient: a primer capable of specifically amplifying a DNA including the nucleotide sequence set out in SEQ ID NO: 2, or a part or all of the DNA of the expression control region thereof; or the antibody or the antibody fragment according to the sixth aspect.

In a twelfth aspect, provided is a screening method for a compound candidate for a therapeutic drug for a disease derived from an abnormality in the neuromuscular junction, including the steps of:

bringing a polypeptide including an amino acid sequence having the substitution, deletion and/or addition of one or several amino acid residues in the amino acid sequence set out in SEQ ID NO: 1, into contact with a test substance; and detecting binding of the polypeptide with the test substance.

In a thirteenth aspect, provided is a screening method for a compound candidate for a therapeutic drug for a disease derived from an abnormality in the neuromuscular junction, including the steps of:

bringing a muscle-specific tyrosine kinase into contact with a polypeptide having the amino acid sequence set out in SEQ ID NO: 1 or a fragment thereof having a binding activity with a muscle-specific tyrosine kinase, in the presence and absence of a test substance; and comparing the binding activity in the presence of the test substance with the binding activity in the absence of the test substance.

In a fourteenth aspect, provided is a screening method for a compound candidate for a therapeutic drug for a disease derived from an abnormality in the neuromuscular junction, including the steps of:

bringing a test substance into contact with a cell expressing a DNA having the nucleotide sequence set out in SEQ ID NO: 2; and detecting alteration of the amount of expression of the DNA.

In a fifteenth aspect, provided is a screening method for a compound candidate for a therapeutic drug for a disease derived from an abnormality in the neuromuscular junction, including the steps of:

administrating a test substance to the nonhuman transformed animal according to the seventh aspect; and detecting amelioration of the abnormality in the neuromuscular junction in the nonhuman transformed animal.

EFFECTS OF THE INVENTION

According to the DNA and the like in the present invention, the activity of MuSK can be modulated. Thus, neuromuscular transmission disorders can be prevented by the DNA and the like.

BRIEF DESCRIPTION OF THE DRAWINGS

FIG. 3 illustrates the localization of the polypeptide of the present invention;

FIG. 11 illustrates the localization of mRNA of the gene of the present invention;

FIG. 25 illustrates the interaction of the polypeptide of the present invention with a muscle-specific tyrosine kinase; and FIG. 26 illustrates an N-terminal region of the polypeptide of the present invention, and a homologous protein thereof. (SEQ ID NO: 4, SEQ ID NO: 5, SEQ ID NO: 6).

PREFERRED MODE FOR CARRYING OUT THE INVENTION

Figure 1:
FIG. 1 illustrates the amount of transcription of the DNA of the present invention in each organ.

Hereinafter, the embodiments of the present invention are explained.

DNA

The term "DNA" herein may be either a sense strand or an antisense strand (for example, one which can be used as a probe), and the form may be either single stranded or double stranded. Also, it may be either a genomic DNA or a cDNA, or alternatively may be a synthesized DNA.

The DNA according to the most preferred embodiment of the present invention is a DNA having the nucleotide sequence set out in SEQ ID NO: 2, and the DNA of the present invention may further include a variety of mutants and homologues that modulate the activity of a muscle-specific tyrosine kinase. Herein, to "modulate the activity of a muscle-specific tyrosine kinase" may include improving the activity of a muscle-specific tyrosine kinase (i.e., activation), and suppressing the same. The phrase "activation of a muscle-specific tyrosine kinase" means capable of phosphorylating tyrosine in a muscle-specific tyrosine kinase molecule, and/or accelerating clustering of AChR.

The mutants and homologues of the DNA having the nucleotide sequence set out in SEQ ID NO: 2 include, for example, DNAs having a nucleotide sequence which can hybridize with the nucleotide sequence set out in SEQ ID NO: 2 under stringent conditions. The "stringent conditions" herein may include, for example, conditions of allowing a reaction in a common hybridization buffer at 40 to 70° C. (preferably, 60 to 65° C.), and washing in a washing fluid having a salt concentration of 15 to 300 mM (preferably, 15 to 60 mM).

In addition, DNAs including a nucleotide sequence encoding an amino acid sequence having the substitution, deletion and/or addition of one or several amino acid residues in the amino acid sequence set out in SEQ ID NO: 1 are also included in the present invention. Herein, the term "one or several" means usually within 50 amino acids, preferably within 30 amino acids, more preferably within 10 amino acids (for example, within 5 amino acids, within 3 amino acids, and 1 amino acid). For maintaining the ability to activate a muscle-specific tyrosine kinase, the mutation of the amino acid residue is preferably conducted with another amino acid having a conserved property of the amino acid side chain. For example, in terms of the property of the amino acid side chains, the amino acids include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxyl group-containing side chain (S, T, Y), amino acids having a sulfur atom-containing side chain (C, M), amino acids having a carboxylic acid and an amide-containing side chain (D, N, E, Q), amino acids having a base-containing side chain (R, K, H), and amino acids having an aromatic group-containing side chain (H, F, Y, W). In the parentheses, each represents one-letter code for the amino acid.

It has been already known that proteins having an amino acid sequence modified by deletion or addition of one or several amino acid residues, and/or substitution with other amino acid in a certain amino acid sequence maintain their original biological activity (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

According to one preferred embodiment of the DNA of the present invention, the DNA encodes a polypeptide that has the substitution, deletion and/or addition of one or several amino acid residues in the amino acid sequence of positions 1 to 230 set out in SEQ ID NO: 1 (but has the amino acid sequence of positions 1 to 60 set out in SEQ ID NO: 1), and that modulates the activity of a muscle-specific tyrosine kinase.

Furthermore, the mutants and homologues of the DNA having the nucleotide sequence set out in SEQ ID NO: 2 include DNAs including a nucleotide sequence that has high homology to the nucleotide sequence set out in SEQ ID NO: 2. Such DNAs have homology of preferably 90% or higher, and more preferably 95% or higher (96% or higher, 97% or higher, 98% or higher, or 99% or higher) to the nucleotide sequence set out in SEQ ID NO: 2 of Sequence Listing. The homology of the amino acid sequence and the nucleotide sequence can be determined with the BLAST algorithm (Proc. Natl. Acad. Sci. USA 90: 5873-5877, 1993) by Karlin and Altschul. On the basis of this algorithm, programs named BLASTN, BLASTX etc. have been developed (Altschul et al. J. Mol. Biol. 215: 403-410, 1990). When the nucleotide sequence is analyzed with BLASTN on the basis of BLAST, the parameter may include, for example, score=100, and wordlength=12. Alternatively, when the amino acid sequence is analyzed with BLASTX on the basis of BLAST, the parameter may include, for example, score=50, and wordlength=3. When BLAST and Gapped BLAST program are employed, default parameters of each program may be used. Specific processes in these analysis method have been known (http://www.ncbi.nlm.nih.gov.).

The method for obtaining the DNA of the present invention is not particularly limited, and includes known methods such as methods for obtaining a cDNA by reverse transcription from a mRNA (for example, RT-PCR method), methods of preparing from a genomic DNA, methods of synthesizing by chemical synthesis, methods of isolating from a genomic DNA library or a cDNA library, and the like (see, for example, Japanese Unexamined Patent Application, First Publication No. Hei 11-29599).

Vector

The vector of the present invention can be produced by inserting the DNA described above into an adequate vector.

The "adequate vector" may be one capable of self-proliferating or keeping replicating in a variety of host of a prokaryotic organism and/or eukaryotic organism, and can be selected appropriately depending on the intended use thereof. For example, when obtaining a large amount of the DNA is desired, a high-copy vector can be selected, whereas an expression vector can be selected when obtaining a polypeptide is intended. The vector is not particularly limited, and specific examples include, e.g., known vectors such as those disclosed in Japanese Unexamined Patent Application, First Publication No. Hei 11-29599.

Transformant

The transformant of the present invention can be produced by introducing the vector including the DNA described above into a host.

Such a host is not particularly limited as long as it is compatible with and can be transformed with the vector of the present invention, and specific examples thereof include known naturally occurring cells such as bacteria, yeast, animal cells and insect cells, as well as artificially established cells (see, Japanese Unexamined Patent Application, First Publication No. Hei 11-29599).

The method for introducing the vector may be selected appropriately depending on the type of the vector, the host, and the like. Specific examples of the method include known methods such as a protoplast method, a competent method, and the like (see, for example, Japanese Unexamined Patent Application, First Publication No. Hei 11-29599), but not particularly limited thereto.

Polypeptide

The polypeptide of the present invention can be produced using, for example, a transformant into which an expression vector including the DNA described above was introduced. In other words, the transformant is first cultured under appropriate conditions, whereby the protein (polypeptide) encoded by this DNA is synthesized. Accordingly, the polypeptide of the present invention can be obtained by recovering the synthesized protein from the transformant or culture fluid.

The transformant can be cultured through appropriately selecting a known nutrient medium depending on the type of the transformant and the like such that the polypeptide can be readily obtained in a large amount, and then appropriately adjusting the temperature, pH, culture time and the like of the nutrient medium (see, for example, Japanese Unexamined Patent Application, First Publication No. Hei 11-29599).

The method of isolation and the method of purification of the polypeptide are not particularly limited, and examples thereof include known methods such as a method in which solubility is utilized, a method in which the difference in the molecular weight is utilized, a method in which the charging is utilized, and the like (see, for example, Japanese Unexamined Patent Application, First Publication No. Hei 11-29599).

Antibody, Antibody Fragment

The antibody or the antibody fragment of the present invention binds to the polypeptide of the present invention described above.

The antibody of the present invention may be either a polyclonal antibody, or a monoclonal antibody. Moreover, the antibody includes antisera obtained by immunizing an animal for immunization such as a rabbit with the polypeptide of the present invention, polyclonal antibodies and monoclonal antibodies in all classes, human antibodies and humanized antibodies prepared by gene recombination, and variously modified antibodies.

The method for producing the antibody of the present invention includes, for example, a conventionally known hybridoma technique (Kohler and Milstein, Nature 256: 495 (1975)).

In addition, the antibody fragment of the present invention includes Fab, F (ab')2, Fv, or single chain Fv (scfv) in which Fv of an H chain and an L chain are linked with a suitable linker (Huston, J. S. et al., Proc. Natl. Acad. Sci. U.S.A. (1988) 85, 5879-5883).

Pharmaceutical Composition

The pharmaceutical composition of the present invention can be produced by blending the aforementioned DNA and/or polypeptide as an active ingredient.

According to this pharmaceutical composition, since the DNA and/or polypeptide is included as an active ingredient, MuSK can be activated, and thus formation of a high-AChR density site can be accelerated. Therefore, this pharmaceutical composition can be used as a therapeutic drug or a prophylactic drug for a disease derived from an abnormality in the neuromuscular junction (for example, congenital myasthenic syndrome). See, Examples described later.

The pharmaceutical composition of the present invention can be administered orally or parenterally (for example, direct administration into muscle by injection). The amount of administration should be selected appropriately since it may vary depending on the age, sex, body weight and symptoms of the patient, treatment effect, administration method, treatment time, and the like.

The phrase "including as an active ingredient" means to contain to an extent that is effective as a therapeutic medical drug or a prophylactic medical drug for a neuromuscular transmission disorder, but does not exclude to contain other arbitrary ingredient.

The other arbitrary ingredient is not particularly limited, and examples thereof include carriers such as excipients, diluents, thickening agents, disintegrants, stabilizers, preservatives, buffering agents, emulsifying agents, aromatic agents, colorants, edulcorants, thickening agents and solubilizing agents, and the like. With these arbitrary ingredients, pharmaceutical compositions in a variety of forms such as tablet, pill, powdered formulation, granule, injectable agent, liquid formulation, capsule, lozenge, elixir and the like can be readily prepared.

Transformed Animal

A nonhuman transformed animal can be produced by introducing, mutating, or knocking out the DNA of the present invention in a nonhuman animal.

Since the DNA of the present invention is introduced, mutated, or knocked out in such a nonhuman transformed animal, the mode of gene expression in the animal body is changed. Thus, this transformed animal can be used as a means for analyzing the function of the DNA of the present invention in animal bodies, a system for screening a substance that regulates this function, and the like.

The nonhuman animal is not particularly limited, and examples thereof include mouse, rat, guinea pig, hamster, rabbit, goat, pig, dog, cat and the like.

The method for producing the nonhuman transformed animal may be, for example, as in the following. First, the DNA of the present invention, a mutant of the DNA, or a DNA homologously recombined with the DNA is introduced into a fertilized ovum of a nonhuman mammalian animal. Then, the fertilized ovum is transplanted into a female individual uterus to permit development, whereby a nonhuman transformed animal in which the DNA of the present invention is transformed can be produced.

More specifically, the production of the nonhuman transformed animal can be carried out, for example, as follows.

First, a female individual after allowing for superovulation by administration of a hormone is mated to a male. Next, the fertilized ova are extirpated from the oviduct of the female individual one day after the mating, and a vector including the DNA of the present invention, a DNA of the mutant, or a DNA homologously recombined with the DNA is introduced into these fertilized ova by a process such as microinjection. Then, after the fertilized ova following the introduction are cultured by a proper process, the surviving fertilized ovum is transplanted into the uterus of a pseudopregnant female individual (foster parent), and delivery of a new born animal is allowed. Whether or not transformation with the DNA was perfected in this new born animal can be ascertained by a Southern analysis of the DNA extracted from the cells of this new born animal.

Alternatively, the nonhuman transformed animal may be also produced by: carrying out gene transfer and selection in an embryonic stem cell (ES cell) strain; then producing a chimeric animal that is responsible for a germ cell line; and mating.

Test Method, Test Agent

The DNA of the present invention can be used in tests on the presence/absence of morbidity of a disease derived from an abnormality in the neuromuscular junction (for example, congenital myasthenic syndrome).

More specifically, the test method for a disease derived from an abnormality in the neuromuscular junction (for example, congenital myasthenic syndrome) includes the steps of: extracting the DNA from the cell of a subject; amplifying the extracted DNA as a template by performing a polymerase chain reaction using a primer capable of specifically amplifying a DNA including the nucleotide sequence set out in SEQ ID NO: 2, or a part or all of the DNA of the expression control region thereof; reading the nucleotide sequence of the amplified DNA; and comparing the read nucleotide sequence with the nucleotide sequence set out in SEQ ID NO: 2.

According to this test method, the DNA nucleotide sequence of Dok-7 gene in a suspect for a congenital myasthenic syndrome is compared with the DNA nucleotide sequence of the Dok-7 gene (set out in SEQ ID NO: 2) in a normal individual. As a result of such comparison, it can be decided that the suspect is suffering from a disease derived from an abnormality in the neuromuscular junction (for example, congenital myasthenic syndrome) when the DNA nucleotide sequence of the Dok-7 gene in the suspect is different from the DNA nucleotide sequence of the Dok-7 gene (set out in SEQ ID NO: 2) in the normal individual.

Moreover, the test method of the present invention may also include the step of decision by, for example, introducing the DNA amplified in the amplification step into a myotube (for example, wild type myotube, MuSK-deficient myotube) or the like, and deciding whether or not the muscle-specific tyrosine kinase is activated. Accordingly, the test accuracy is improved since the case in which the difference between the nucleotide sequence of the amplified DNA and the nucleotide sequence set out in SEQ ID NO: 2 merely results from a polymorphism, and the like can be excluded.

In this test method, a nucleotide sequence of a gene which has been already known to participate in congenital myasthenic syndrome (choline acetyl transferase, AChRs, acetylcholine esterase, Rapsyn, MuSK or the like) may be also compared together, in addition to the Dok-7 gene. Thus, the accuracy of diagnosis of the congenital myasthenic syndrome can be further improved (see, for example, A. G. Engel and S. M. Sine, "Current Opinion Pharmacology", 5, 308 (2005)).

Other test method includes the steps of: determining the amount of expression of a DNA having the nucleotide sequence set out in SEQ ID NO: 2 in the cell of a subject; and comparing the determined amount of expression of the DNA with the amount of expression of the DNA set out in SEQ ID NO: 2 in a healthy individual.

Herein, "expression of the DNA" involves both expression at a transcription level (mRNA expression) and a translation level (protein expression).

According to this test method, the amount of expression of a DNA having the nucleotide sequence set out in SEQ ID NO: 2 is compared between a subject and a healthy individual. As a result of such comparison, it can be decided that the suspect is suffering from a disease derived from an abnormality in the neuromuscular junction (for example, congenital myasthenic syndrome) when the amount of expression of the DNA in the subject is significantly different from the amount of expression of the DNA in the healthy individual.

Moreover, the test agent for the disease derived from an abnormality in the neuromuscular junction (for example, congenital myasthenic syndrome) includes as an active ingredient a primer capable of specifically amplifying the DNA having a part or entirety of the nucleotide sequence set out in SEQ ID NO: 2, or the antibody or the antibody fragment described above.

Screening Method for Compound Candidate for Therapeutic Drug

The polypeptide of the present invention can be used in a screening method for a compound candidate for a therapeutic drug for a disease derived from an abnormality in the neuromuscular junction (for example, congenital myasthenic syndrome).

More specifically, the screening method includes the steps of bringing the aforementioned polypeptide into contact with a test substance, and detecting binding of the polypeptide with the test substance.

According to this screening method, the test substance detected to bind to the polypeptide can be specified as a compound for candidate for a therapeutic drug.

Moreover, another screening method includes the steps of: bringing a muscle-specific tyrosine kinase into contact with a polypeptide having the amino acid sequence set out in SEQ ID NO: 1 or a fragment thereof having a binding activity with a muscle-specific tyrosine kinase in the presence and absence of a test substance; and comparing the binding activity in the presence of the test substance with the binding activity in the absence of the test substance.

According to this screening method, a test substance detected as exhibiting a different binding activity with a binding material in the presence of the test substance from a binding activity with the binding material in the absence of the test substance can be specified as a compound candidate for a therapeutic drug.

Furthermore, another screening method includes the steps of: bringing a test substance into contact with a cell that expresses a DNA having the nucleotide sequence set out in SEQ ID NO: 2; and detecting alteration of the amount of expression of the DNA.

Herein, the phrase "expression of the DNA" involves both expression at a transcription level (mRNA expression) and a translation level (protein expression).

According to this screening method, a test substance detected as leading alteration of the amount of expression of the intracellular DNA can be specified as a compound candidate for a therapeutic drug.

Additionally, another screening method includes the steps of: administrating a test substance to the aforementioned nonhuman transformed animal; and detecting amelioration of an abnormality in the neuromuscular junction in the nonhuman transformed animal.

According to this screening method, a test substance found to exhibit amelioration of an abnormality in the neuromuscular junction in the nonhuman transformed animal can be specified as a compound candidate for a therapeutic drug.

A kit for screening which may be used in the foregoing screening method includes the polypeptide of the present invention. In addition, the present invention also involves compounds candidate for a therapeutic drug specified by the foregoing screening method.

Others

[Recording Medium]

The nucleotide sequence of the DNA, and the amino acid sequence of the polypeptide may be stored in a computer-readable recording medium. This recording medium enables a database of the stored amino acid sequence of the polypeptide, and nucleotide sequence of the DNA of the present invention to be compiled using a computer. Accordingly, the amino acid sequence and the nucleotide sequence can be utilized also as sequence information.

The recording medium is not particularly limited as long as it is computer-readable, and examples thereof include magnetic media such as flexible disks, hard disks and magnetic tapes, optical disks such as CD-ROM, MO, CD-R, CD-RW, DVD-R and DVD-RAM, semiconductor memories, and the like.

[Tool for Comprehensive Analysis]

The DNA and the polypeptide of the present invention, and a partial fragment of the same can be also used in the state being bound as a carrier on a substrate. The substrate to which other polypeptide or DNA is further bound in addition to the polypeptide or DNA of the present invention can be used in a comprehensive analysis involving the polypeptide or DNA of the present invention.

The substrate is not particularly limited, and examples thereof include resin substrates such as a nylon membrane and a polypropylene membrane, nitrocellulose membranes, glass plates, silicon plates, and the like. Furthermore, when detection of hybridization is conducted using a nonradioactive isotope substance such as, for example, a fluorescent substance, a glass plate, a silicon plate or the like without including a fluorescent substance can be preferably used as a substrate.

Binding of the polypeptide or the DNA on the substrate can be permitted by a known method.

EXAMPLES

Example 1

Production of cDNA

First, an amino acid sequence (constituted with about 100 amino acid residues) of a PTB domain highly conserved among Dok family molecules was entered in a known database (for example, BLAST Search of NCBI), and a clone having high homology was searched. Based on the positional information of translation initiation codon and translation termination codon in the sequence information of the clone found as a result of this search, ORF (nucleotide sequence region encoding the protein) of Dok-7 was predicted. Then, based on the nucleotide sequence information of the ORF, the oligo primer shown below was designed, and the cDNA corresponding to the human Dok-7 ORF region was isolated with a PCR method according to a common procedure. The nucleotide sequence of the isolated full length cDNA was read by a known method, and revealed the nucleotide sequence set out in SEQ ID NO: 2 in Sequence Listing.

(SEQ ID NO: 7)
5'-atgaccgaggcggcgctggtgg-3'.

(SEQ ID NO: 8)
5'-tcaaggaggggggtttaccttg-3'

Example 2

Production of cDNA Insert Vector

Thus resulting cDNA was inserted into "pcDNA3.1 (trade name)" (manufactured by Clontech) and "pcDNA3.1-myc/His (trade name)" (manufactured by Clontech), "pEGFP-N3 plasmid" (manufactured by Clontech) which are expression vectors for mammalian animal cells, and "pGEX-4T-2" (manufactured by Amersham Pharmacia) which is an expression vector for *Escherichia coli* cells, at the open reading frame which can produce the polypeptide having the amino acid sequence set out in SEQ ID NO: 1.

This insertion was carried out by a well-known method including the steps of: performing PCR using a primer designed such that a restriction site was added to match the restriction enzyme site within the multicloning site of the vector to be inserted; subjecting the amplified product after the PCR and the vector to a treatment with a restriction enzyme; subjecting the amplified product and the vector treated with the restriction enzyme to a treatment with ligase; transforming the vector treated with ligase into *Escherichia coli*; culturing the transformed *Escherichia coli* for a predetermined time; and purifying the vector from the *Escherichia coli* following the culture.

With "pcDNA3.1-myc/His", the polypeptide can be synthesized in the form including a polyhistidine tag fused at its N-terminal, and a FLAG tag and a myc tag fused at its C-terminal. Alternatively, with "pEGFP-N3 plasmid", the polypeptide is synthesized in the form including an enhanced green fluorescent protein (EGFP) fused at its C-terminal. Also, with "pGEX-4T-2" (manufactured by Amersham Pharmacia), the polypeptide is synthesized in the form including a glutathione-S-transferase (hereinafter, may be also referred to as "GST") tag fused at its N-terminal. These tags and epitopes may be removed appropriately by carrying out, for example, an enzymatic treatment, depending on use after the synthesis.

Example 3

Production of Transformant

A transformed C2 myogenic cell strain was produced according to the following procedure. More specifically, a C2 myogenic cell strain (C2C12) obtained from ATCC (American Type Culture Collection) was cultured first in Dulbecco's Modified Eagle's (DME) medium supplemented with 20% by volume of fetal bovine serum (FBS). Next, a transformant was produced by introducing "pcDNA3.1-myc/His" that includes the DNA of the present invention described above into the C2 myogenic cell strain cultured to give an adequate number of the cells using "Lipofectamine 2000" (manufactured by Invitrogen Corporation).

Furthermore, a transformed 293T cell strain was produced according to the following procedure. More specifically, a 293T cell strain that is a human culture cell (nonmuscle cell) was cultured first in DME medium supplemented with 10% by volume of FBS. Next, a transformant was produced by introducing "pcDNA3.1-myc/His" that includes the aforementioned DNA into the 293T cell strain cultured to give an adequate number of the cells using "Lipofectamine 2000" (manufactured by Invitrogen Corporation).

Further, a transformed *Escherichia coli* was produced according to the following procedure. More specifically, *Escherichia coli* was first cultured in LB medium until an appropriate bacterial concentration was achieved, and thereto was introduced "pGEX-4T-2" including the aforementioned DNA according to a well-known heat shock method, whereby a transformant was produced.

Example 4

Production of Polypeptide

The polypeptide of the present invention was produced according to the following procedure. More specifically, the aforementioned transformed *Escherichia coli* was first cultured in LB medium until an appropriate bacterial concentration was achieved, and the bacterial bodies following the culture were collected by centrifugal separation. Next, after the collected bacterial bodies were suspended in a 50 mM phosphate buffer (pH 8.0), the cell wall was disrupted by ultrasonication. Subsequently, the disrupted matter was centrifuged to obtain a membrane fraction containing the protein of interest. Then, this membrane fraction was solubilized with a surfactant "TritonX-100" to prepare a crude solution, from which the protein of interest was isolated and purified according to a common procedure using Glutathione Sepharose (Amersham Pharmacia).

Example 5

Production of Antibody

A fusion protein of glutathione S transferase with the human Dok-7 polypeptide fragment (including the amino acid sequence of positions 214 to 291 set out in SEQ ID NO: 1 in Sequence Listing) produced by the aforementioned method was injected as an antigen into a rabbit and a rat, respectively, to obtain anti-Dok-7 antisera. It was proven from the results of western analyses that the antiserum recognized the Dok-7 protein derived from human, mouse, and rat, but did not recognize the Dok-7 protein derived from Fugu rubripe (not shown in the Figure).

Example 6

Analysis of Dok-7 Gene (A) Localization of mRNA of Dok-7 Gene

In order to analyze general localization of the mRNA of the Dok-7 gene, a Northern analysis was performed according to a common procedure using an RNA blot extracted from each human brain, heart, skeletal muscle, large intestine, thymus, spleen, kidney, liver, small intestine, placenta, lung, and peripheral leukocyte (corresponding in this order to 1 to 12 each in FIG. 1) as an analyte ("Human Multi Tissue Blot" (manufactured by Clontech) employed). The results are shown in FIG. 1.

As shown in FIG. 1, the transcriptional activity of the human Dok-7 gene was detected only in the heart and skeletal muscle. At the bottom part of FIG. 1, results of analysis of β-actin (control plot) are shown.

(B) Localization of Dok-7 Protein

In order to analyze general localization of the Dok-7 protein, a western analysis was performed according to a common procedure using proteins extracted from mouse cardiac muscle (CM), thigh muscle (TM), liver (Lv), spleen (Sp), and diaphragmatic muscle (DM), respectively, as analytes. The antibodies used in the western analysis were an anti-Dok-7 antiserum, and an anti-β-actin antibody "I-19" (manufactured by Santa Cruz Biotechnology, Inc.). The results are shown in FIG. 2.

Figure 2:
FIG. 2 illustrates the amount of expression of the polypeptide of the present invention in each organ.

As shown in FIG. 2, the mouse Dok-7 protein was detected only in the cardiac muscle, and skeletal muscle (thigh muscle and diaphragmatic muscle). At the bottom part of FIG. 2, results of analysis (control plot) of β-actin are shown.

Next, in order to analyze localization of the Dok-7 protein at a cellular level, immunostaining was carried out around the postsynaptic region of a muscle-neuromuscular junction in mouse gastrocnemial muscle prior to and post ischiatic nerve resection according to a common procedure. The antibodies used in the immunostaining were an anti-Dok-7 antiserum, and an anti-synaptophysin antibody "SVP38" (manufactured by Santa Cruz Biotechnology, Inc.).

Synaptophysin (SYN) is a component of presynaptic vesicle, and represents a control plot showing the position of the presynaptic region and the like. Bungarotoxin (Btx) represents a control plot showing the position of AChR. The results are shown in FIG. 3. The results obtained when the tissue prior to the ischiatic nerve resection was used are shown in the left panels in FIG. 3, while the results obtained when the tissue one week after the ischiatic nerve resection was used are shown in the right panels in FIG. 3. Although the overlapped figure illustrating both Dok-7 and Btx is not shown, each drawing in left and right panels in FIG. 3 was taken at the same field of the same section. Also, the bar in FIG. 3 corresponds to the size of 20 μm.

As shown in FIG. 3, synaptophysin disappeared after the ischiatic nerve resection. To the contrary, the Dok-7 protein colocalized with AChR, and this colocalization was retained throughout, before and after the nerve resection.

From the foregoing results, it was suggested that Dok-7 was a protein expressed not in nerve but in muscle, and had a function relating to AChR in the postsynaptic region of neuromuscular junction.

Example 7

Characterization of Dok-7 Protein Function

Examples showing interaction of phosphorylated tyrosine kinase with a PTB domain present in the molecule of proteins belonging to Dok family have been reported (see, F. Cong, B. Yuan and S. P. Goff, Mol. Cell. Biol. 19, 8314 (1999); J. Grimm et al., J. Cell Biol. 154, 345 (2001); R. J. Crowder, H. Enomoto, M. Yang, E. M. Jr. Johnson and J. Milbrandt, J. Biol. Chem. 279, 42072 (2004), and the like). Furthermore, it was reported that a PTB domain target motif constituted with four amino acids NPXY (positions 550 to 553 set out in SEQ ID NO: 1 of Sequence Listing) in the MuSK molecule is essential for the MuSK activation (see, H. Zhou, D. J. Glass, G. D. Yancopoulos, & J. R. Sanes, J. Cell Biol. 146, 1133 (1999); R. Herbst and S. J. Burden, EMBO J. 19, 67 (2000); R. Herbst, E. Avetisova and S. J. Burden, Development 129, 5449 (2002), and the like). Thus, characterization of the function of the Dok-7 protein was performed through interaction of the Dok-7 protein with MuSK.

(A) Nonmuscle Cell

A vector into which each DNA of a wild type (hereinafter, may be also referred to as "WT") mouse MuSK fused to myc tag, a kinase-inactivated mutated MuSK (hereinafter, may be also referred to as "MuSK-KA") fused to myc tag, or human Dok-7 had been inserted was introduced into the 293T cell strain by the method described above to produce a transformant 293T cell strain. The wild type (WT) mouse MuSK DNA was produced by an RT-PCR method using a primer pair that specifically binds thereto, and the produced DNA was inserted into "pcDNA3.1-myc/His" such that an open reading frame of the desired amino acid sequence is provided according to the aforementioned method. The MuSK-KA DNA was produced by mutating the wild type (WT) mouse MuSK DNA so as to encode an amino acid sequence having the substitution of lysine at position 608 of the amino acid sequence set out in SEQ ID NO: 3 with alanine. This mutation was carried out by a well-known mutation engineering process.

After each of the transformed 293T cells was cultured in DME medium supplemented with 10% by volume of FBS until the number of cells reached a predetermined value, the cells were lysed in an RIPA buffer (50 mM tris-HCl pH 8.0, 150 mM NaCl, 1 mM $Na_3VO_4$, 50 mM NaF, 1% Nonidet P-40, 0.5% sodium deoxycholate, 0.1% SDS) to obtain a whole cell lysate (WCL). Next, this whole cell lysate was subjected to immunoprecipitation according to a common procedure using an anti-myc tag antibody (αmyc) to obtain an immunoprecipitate (IP: αmyc).

Figure 4:
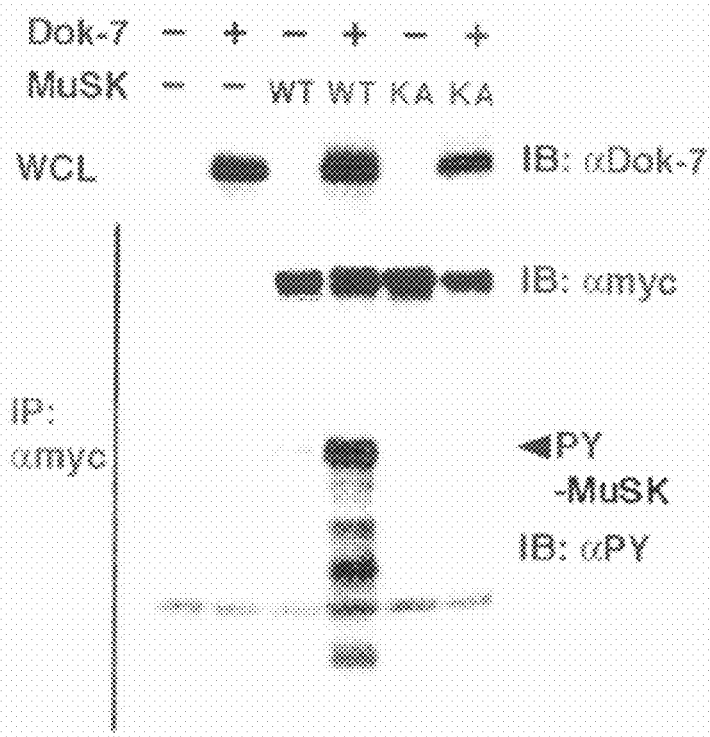
FIG. 4 illustrates the interaction of the polypeptide of the present invention with a muscle-specific tyrosine kinase.

A western analysis was performed for each of the whole cell lysate and immunoprecipitate obtained from each transformant. The Dok-7 antibody (IB: αDok-7) used in the western analysis was a polyclonal antibody purified from a mouse serum immunized with the Dok-7 protein obtained according to the aforementioned procedure. In addition, the anti-phosphorylated tyrosine antibody (IB: αPY) was "4G10" (manufactured by Upstate Biotechnology Inc.), and the anti-myc tag antibody (IB: αmyc) was "9B11" (manufactured by Cell Signaling Inc.). The results are shown in FIG. 4. The upper panel in FIG. 4 shows combinations of the DNAs introduced into each 293T cell used in this analysis.

As shown in FIG. 4, when forced expression of Dok-7 was permitted in the 293T cells, tyrosine phosphorylation of wild type (WT) MuSK was strongly promoted, but the tyrosine phosphorylation of MuSK-KA that is a kinase-inactivated mutant was not detected.

Figure 5:
FIG. 5 illustrates the interaction of the polypeptide of the present invention with a muscle-specific tyrosine kinase.

A western analysis was performed according to a similar procedure, using the transformant 293T cell strain to which each of Fugu rubripe Dok-7 (F7), and human Dok-1 to 7 was introduced. Each of the DNAs of Fugu rubripe Dok-7, human Dok-1 to 6 was produced by an RT-PCR method using a primer pair that specifically binds each thereto, and the produced DNA was inserted into "pcDNA3.1-myc/His" such that an open reading frame of the desired amino acid sequence was provided according to the aforementioned method. The results are shown in FIG. 5. The upper panel in FIG. 5 shows combinations of the DNAs introduced into each 293T cell used in this analysis.

As shown in FIG. 5, the Fugu rubripe Dok-7 protein could promote tyrosine phosphorylation of MuSK, similarly to the human Dok-7 protein. From these results, it was suggested that properties of Dok-7 were common in vertebrates. Meanwhile, in any case of the proteins of human Dok-1 to 6, no tyrosine phosphorylation of MuSK could be detected.

Therefore, it was suggested that Dok-7 was a specific activator of MuSK generally conserved among vertebrates.

(B-1) Myotube

Human C2 myogenic cells transformed with human Dok-7 obtained with the aforementioned procedure was proliferated up to a saturated cell density, and cultured in DME medium supplemented with 2% by volume of equine serum for 5 to 7 days to differentiate to myotube (C2 myotube).

After the C2 myotube was cultured in DME medium supplemented with 2% by volume of equine serum until the number of cells reached predetermined value, the cells were lysed in an alkali solubilization liquid (50 mM tris-HCl pH 9.5, 1 mM $Na_3VO_4$, 50 mM NaF, 1% sodium deoxycholate, 1% Triton-X100) to obtain a whole cell lysate (WCL). Next, this whole cell lysate was subjected to immunoprecipitation according to a common procedure using anti-MuSK antibodies "N-19" and "C-19" (both manufactured by Santa Cruz Biotechnology, Inc.), or to pulling down of the AChR complex with Btx to obtain each immunoprecipitate.

Figure 6:
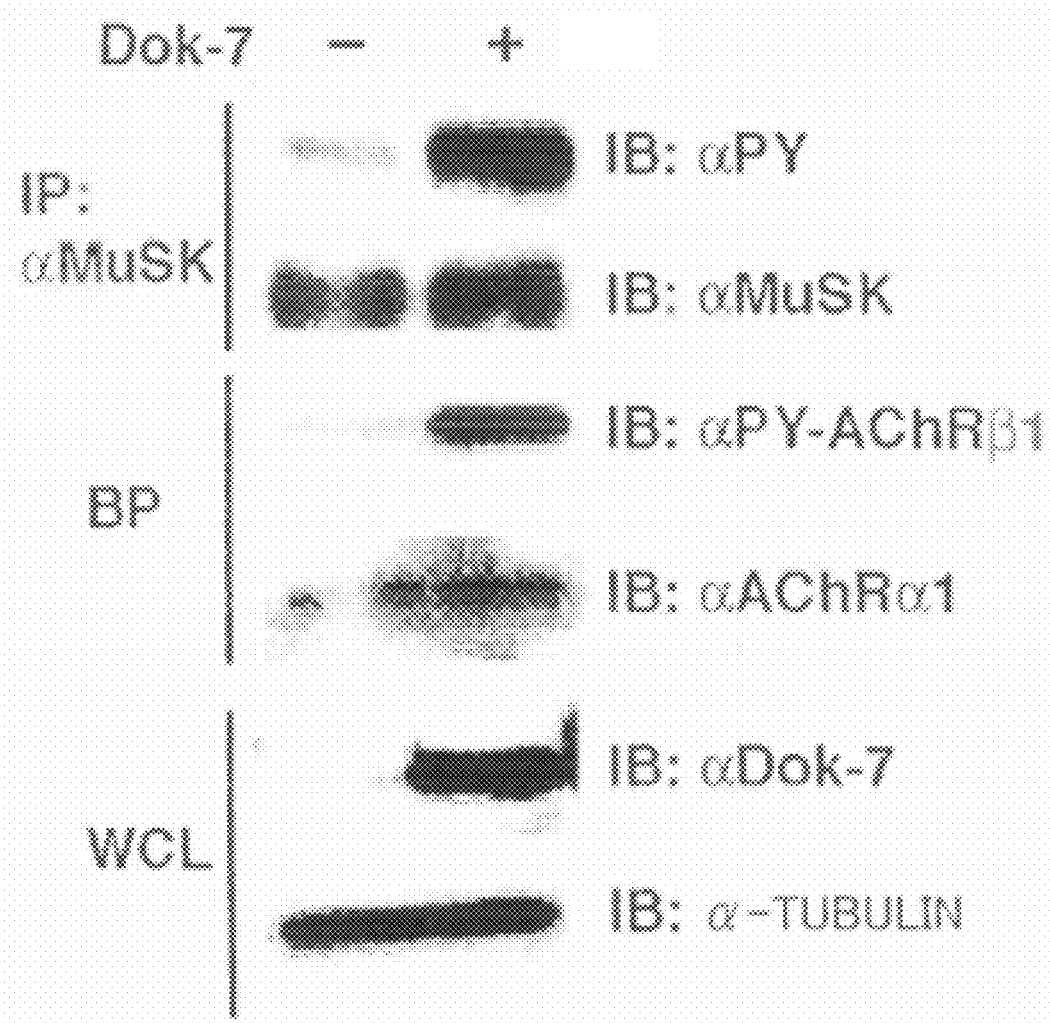
FIG. 6 illustrates the interaction of the polypeptide of the present invention with a muscle-specific tyrosine kinase.

A western analysis was performed for each of the whole cell lysate (WCL) obtained from the C2 myotube, and the immunoprecipitate (IP: αMuSK) obtained by the immunoprecipitation of this whole cell lysate as well as the isolate obtained by the pulling down by Btx (BP). The antibodies used in the western analysis were as follows: an anti-phosphorylated tyrosine antibody (IB: αPY) being "4G10" (manufactured by Upstate Biotechnology Inc.); an anti-MuSK antibody (IB: αMuSK) being "AF562" (manufactured by R&D Systems); an anti-tyrosine phosphorylation AChR β1 antibody being "Tyr-390" (manufactured by Santa Cruz Biotechnology, Inc.); an anti-AChR α1 antibody being "C-18" (manufactured by Santa Cruz Biotechnology, Inc.); a Dok-7 antibody being the aforementioned antiserum (IB: αDok-7); and an α-tubulin antibody (IB: α-tubulin) being "DM1A" (manufactured by Sigma). The results are shown in FIG. 6. The left column in FIG. 6 shows a control plot illustrating the results obtained when "pcDNA3.1-myc/His" without including an insert sequence was introduced into the C2 myogenic cells.

As shown in FIG. 6, when Dok-7 was overexpressed in the myotube, tyrosine phosphorylation of endogenous MuSK was promoted, and tyrosine phosphorylation of AChRβ1 that is the substrate thereof was also promoted.

(B-2) Relationship Between Dok-7 and AChR

The states of clustering of AChR in the C2 myotube transduced with a Dok7-containing plasmid in various amounts were examined according to the following procedure. More specifically, the myotube was first reacted with 1 ng/ml Alexa 594-bound Btx for one hour, washed, and fixed with PBS mixed with 3.7% PFA. Images of the fixed myotube were acquired with "DFC350FX CCD camera" (manufactured by Leica) attached to "DM6000B microscope" (manufactured by Leica). Ten fields observed with objective lens of 40-times magnification were selected randomly, and the number of AChR clusters (diameter: 5 μm or greater) was counted. The results are shown in FIG. 7.

Figure 7:
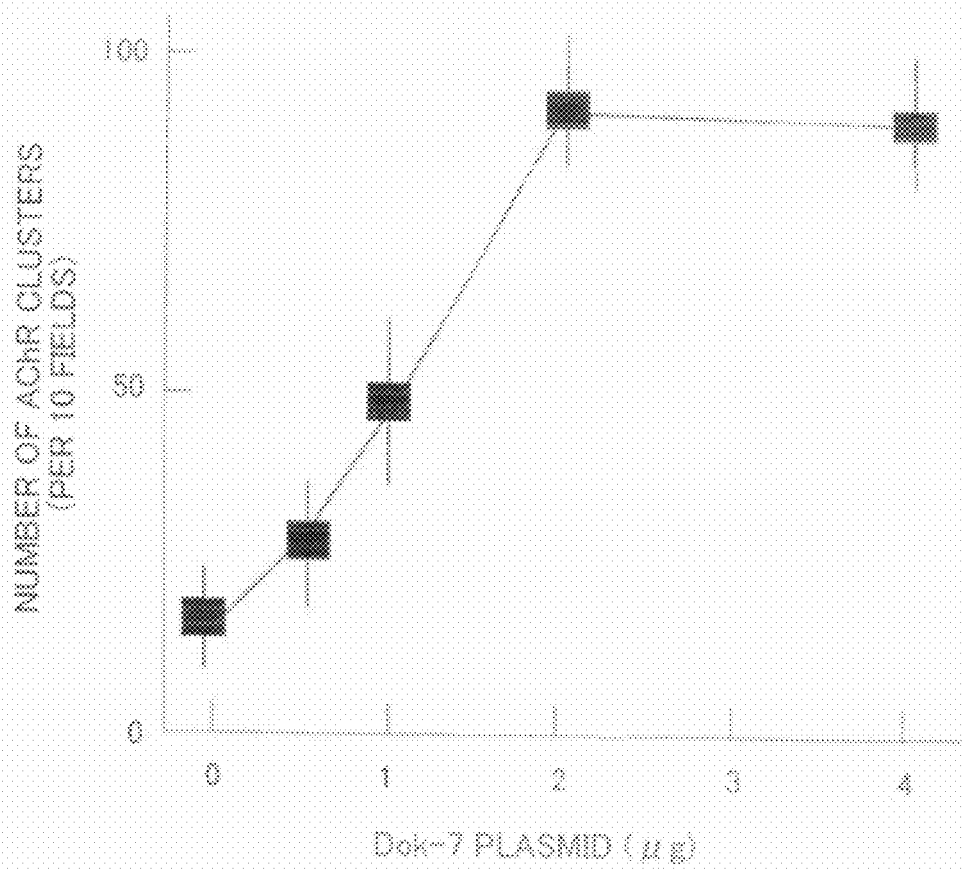
FIG. 7 illustrates the relationship between the amount of the introduced DNA of the present invention and cluster formation of acetylcholine receptors.

As shown in FIG. 7, forced expression of Dok-7 induces AChR clusters, and the number of the AChR clusters correlated with the amount of the Dok-7-containing plasmid introduced.

Figure 8:
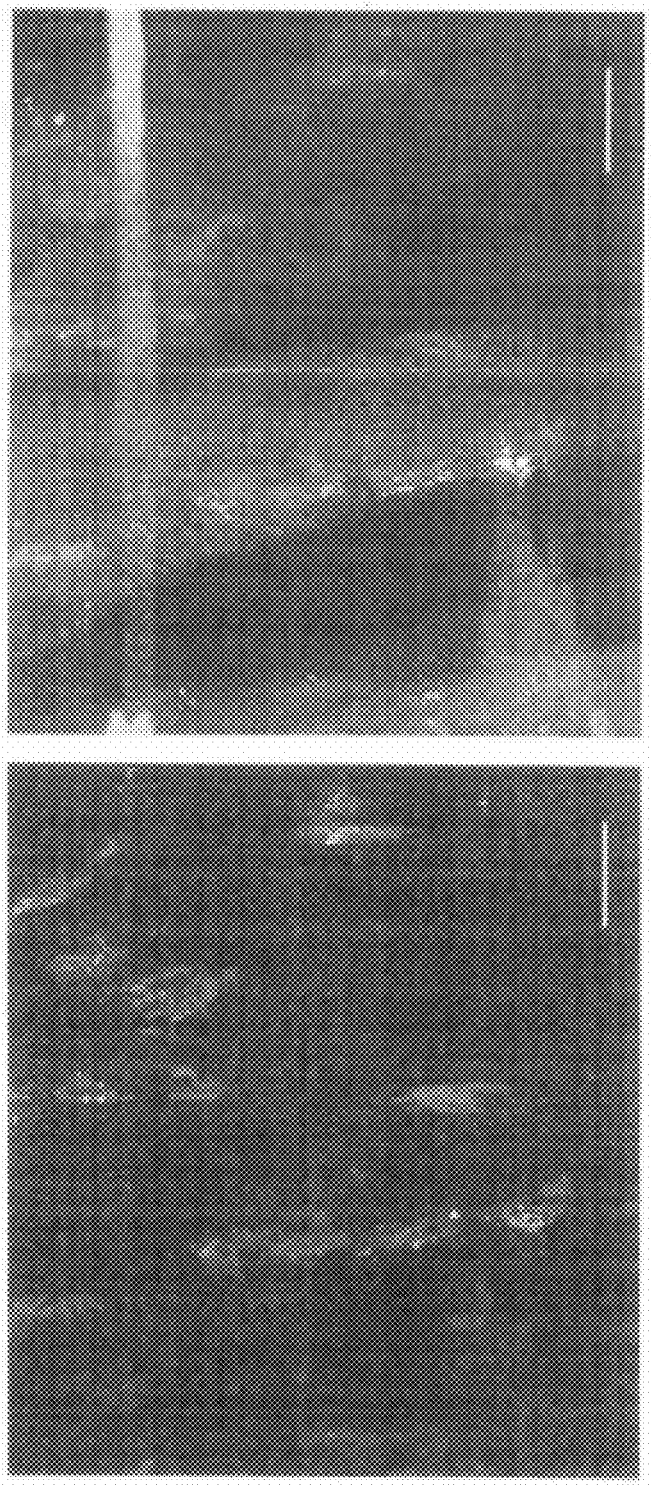
FIG. 8 illustrates the co-cluster formation of the polypeptide of the present invention and acetylcholine receptors.

Next, localization of Dok-7 fused to EGFP when forced expression was permitted in the myotube was investigated together with AChR by confocal microscopic observation. The results are shown in FIG. 8. Although the overlapped figure illustrating both AChR and Dok-7 is not shown, each drawing was taken at the same field of the same section. The bar in FIG. 8 represents the size of 20 μm.

As shown in FIG. 8, Dok-7 yielded by forced expression formed clusters together with AChR. The results agree with the results seen from FIG. 3.

It is also known that AChR forms clusters together with MuSK in the myotube upon activation of MuSK (see, Kummer, T. T., Misgeld, T., Lichtman, J. W. & Sanes, J. R., J. Cell Biol. 164, 1077-1087 (2004); Sander, A., Hesser, B. A. & Witzemann, V. J. Cell Biol. 155, 1287-1296 (2001)).

(B-3) Clustering of AChR

Figure 9:
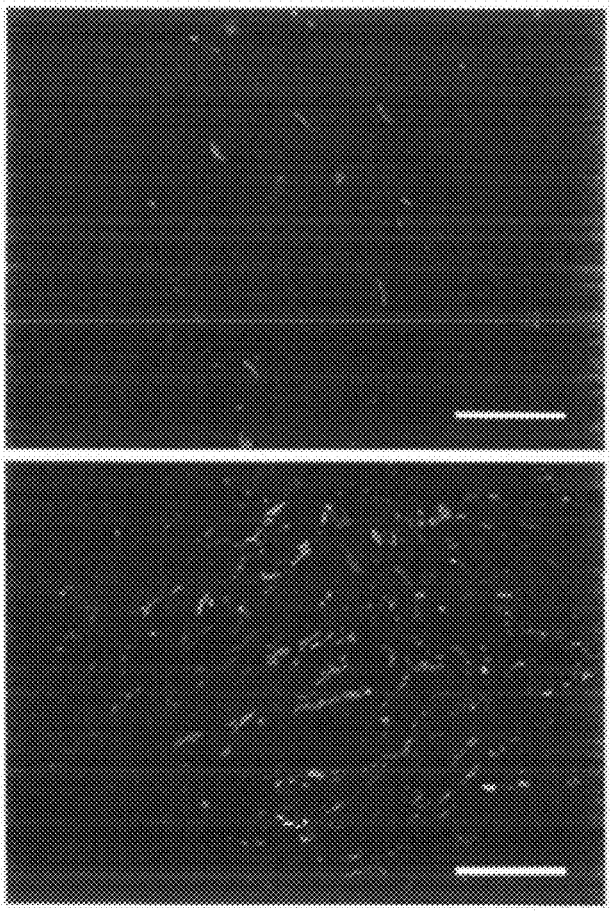
FIG. 9 illustrates the relationship between the expression of the DNA of the present invention and the cluster formation of acetylcholine receptors.

The states of clustering of AChR in C2 myotube to which the aforementioned human Dok-7 was introduced, and C2 myotube to which "pcDNA3.1-myc/His" without including an insert sequence was introduced (control plot) were observed according to the aforementioned procedure. A part of the results are shown in FIG. 9. The bar in FIG. 9 represents the size of 200 μm.

As shown in FIG. 9, significantly more clustering of AChR was observed in the C2 myotube transformed with human Dok-7 in comparison with the control plot. In addition, although not shown in the Figure, significant difference was not observed with respect to the clustering of AChR in the C2 myotube transformed with human Dok-1 to 6, in comparison with the control plot.

It was reported that tyrosine phosphorylation of an AChR β subunit occurs upon activation of MuSK (see, for example, C. Fuhrer, J. E. Sugiyama, R. G. Taylor and Z. W. Hall, EMBO J. 16, 4951 (1997)). In view of this report, the results shown in FIG. 6 and FIG. 9 suggested that the Dok-7 protein promoted tyrosine phosphorylation of AChRβ1 via activation of MuSK, thereby capable of accelerating the clustering of AChR.

Figure 10:
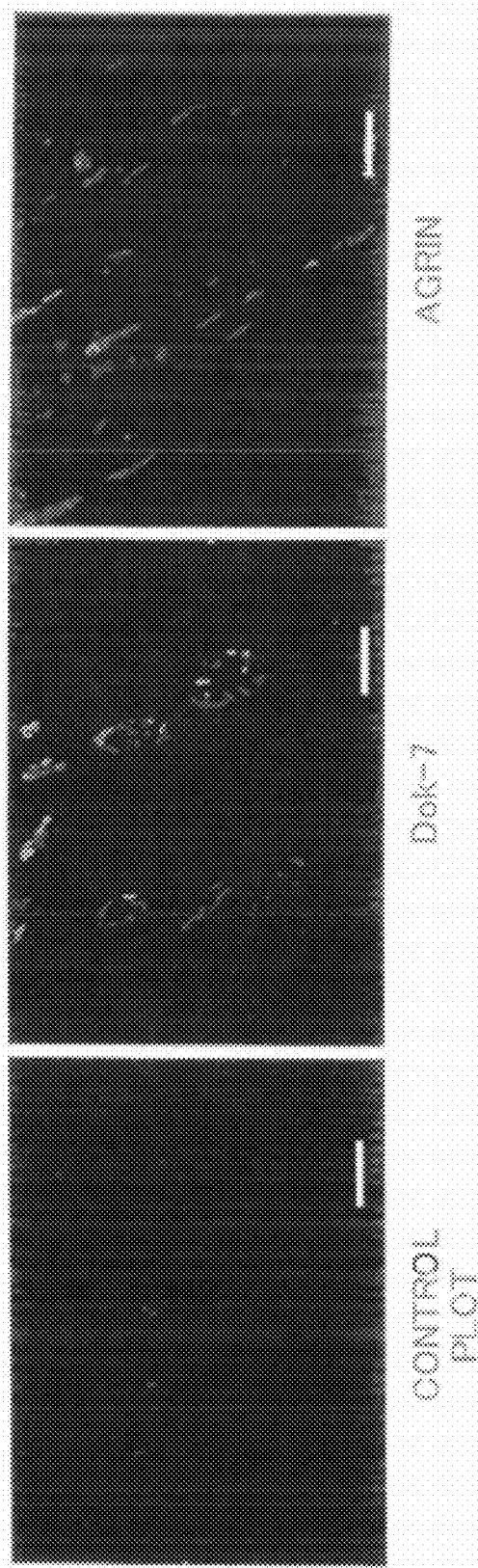
FIG. 10 illustrates the state of cluster formation of the acetylcholine receptors induced by forced expression of the DNA of the present invention.

Next, more detailed observation was carried out on C2 myogenic cells in the process of differentiation, with respect to the transformed C2 myotube as described above, and C2 myogenic cells treated with 10 ng/ml neural agrin for 7 days. The results are shown in FIG. 10. The bar in FIG. 10 represents the size of 40 μm.

As shown in FIG. 10, the site of AChR clustering induced by Dok-7 that is an exogenous gene had a highly branched complicated structure. Furthermore, the site of AChR clustering induced by Dok-7 was greater than the site of clustering induced by agrin, or a spontaneously formed site of clustering. The complicated structure of the observed site of clustering was similar to reported pretzel-like AChR clustering structures observed post differentiation in vitro and in vivo (see, for example, T. T. Kummer, T. Misgeld, J. W. Lichtman and J. R. Sanes, J. Cell. Biol. 164, 1077 (2004)).

Example 8

Localization of Dok-7 mRNA In Vivo

In order to analyze the localization in vivo of the mRNA of the Dok-7 gene in more detail, using the diaphragmatic muscle obtained from mouse embryo of C57BL/6 origin as an analyte, in situ hybridization analysis was performed according to the following procedure.

The diaphragmatic muscle obtained from a mouse embryo was fixed with 4% paraformaldehyde in PBS, treated with proteinase K, and further probed with digoxigenin (DIG)-labeled antisense or sense riboprobe of mouse Dok-7. These probes correspond to nucleotides 1-999 of mouse Dok-7 cDNA (AB220919). In situ hybridization was carried out according to a common procedure, and the signal detected by an alkali phosphatase conjugated anti-DIG antibody was developed by NBT and BCIP. The image was taken using a stereoscopic microscope "MZ16" (manufactured by Leica), equipped with a camera "DP-70" (manufactured by Olympus Corporation). The results are shown in FIG. 11. The bar in FIG. 11 represents the size of 500 μm.

As shown in FIG. 11, the antisense riboprobe specifically bound to the endplate-containing central region of the diaphragm muscles, while no binding of the sense riboprobe was found in this region. Therefore, it was suggested that the mouse Dok-7 mRNA was specifically expressed in the endplate-containing central region of the diaphragm muscles.

Example 9

Analysis of Dok-7 Variant

Using Dok-7 variant and MuSK variant, identification of a site essential for tyrosine phosphorylation of MuSK by the Dok-7 protein was attempted.

(A) MuSK

DNAs that express mutant MuSK (NA and YF) having the mutation in the amino acid sequence (NPXY) of MuSK which was reported to be a target motif of the PTB domain, and tyrosine kinase-inactivated mutant MuSK (KA) were produced by point mutagenesis according to a common procedure. Then, transformant 293T cell strains in which the DNA, and a DNA that expresses wild type Dok-7 are expressed respectively were produced by a similar procedure in the aforementioned method. Herein, NA represents a mutant having the substitution of asparagine at position 550 of the amino acid sequence set out in SEQ ID NO: 3 with alanine; YF represents a mutant having the substitution of tyrosine at position 553 of the amino acid sequence set out in SEQ ID NO: 3 with phenylalanine; and KA represents a mutant having the substitution of lysine at position 608 of the amino acid sequence set out in SEQ ID NO: 3 with alanine. MuSK and its mutants include a fused myc tag.

Figure 12:
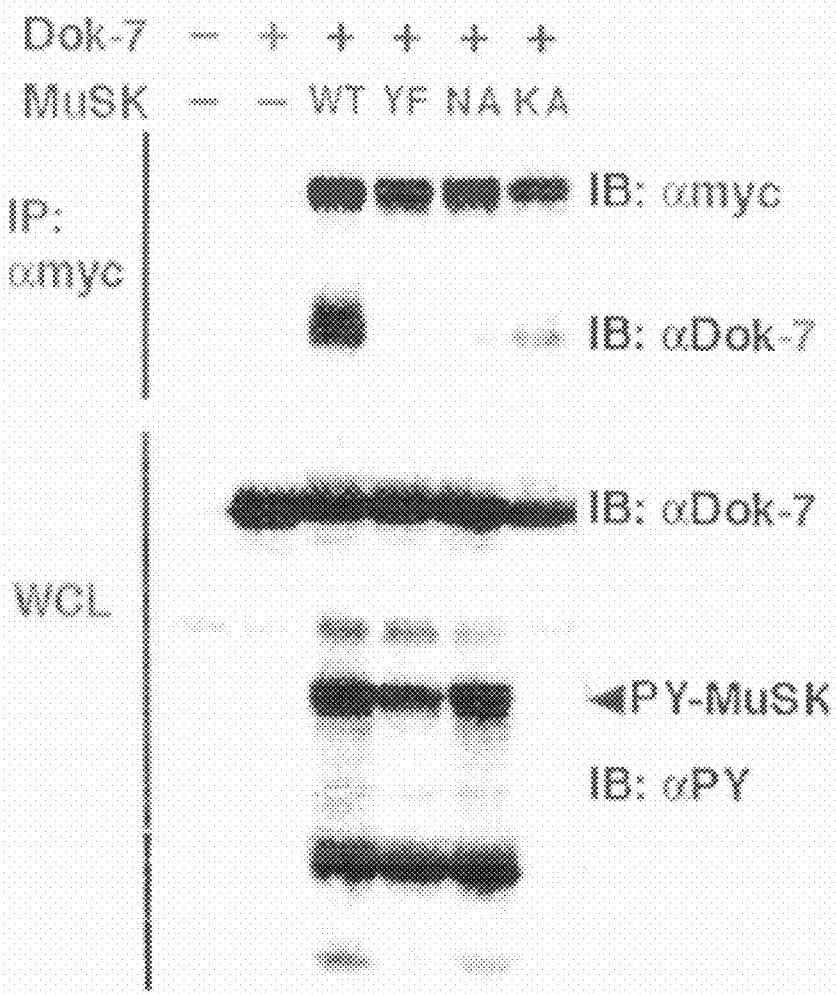
FIG. 12 illustrates the interaction of the polypeptide of the present invention with a muscle-specific tyrosine kinase.

Immunoprecipitation of whole cell lysate (WCL) obtained from each transformed cell strain was carried out using an anti-myc tag antibody, and thus an immunoprecipitate (IP: αmyc) was obtained. Then, a western blot analysis was performed for the whole cell lysate and immunoprecipitate. The antibodies used were the same as the antibodies described above. The results are shown in FIG. 12. The upper part in FIG. 12 shows peptide sequences around the region including a PTB domain target motif for the wild type MuSK, NA mutant, and YF mutant. Moreover, the middle part in FIG. 12 shows combinations of the DNAs introduced into each 293T cell used in this analysis.

As shown in FIG. 12, it was ascertained that the wild type MuSK (WT) bound to and coprecipitated with Dok-7 in 293T cells. In contrast, any of YF and NA was not found to be bound to and coprecipitated with Dok-7. The results suggested that the PTB domain target motif including NPXY was involved in binding of Dok-7 to MuSK. Furthermore, it was also suggested that any of YF and NA did not inhibit tyrosine phosphorylation of MuSK induced by Dok-7 in 293T cells.

(B) Dok-7

First, transformant 293T cell strains were produced by a similar procedure in the aforementioned method, in which wild type human Dok-7 (WT), mutant Dok-7 (ΔN) having the deletion of a part of the PH domain present at the N-terminal side (positions 8 to 107 of the amino acid sequence set out in SEQ ID NO: 1) of the wild type human Dok-7, and mutant Dok-7 (ΔC) having the deletion of a C-terminal side region of the wild type human Dok-7 were expressed respectively, and in which forced expression of MuSK was permitted. Herein, ΔN represents a mutant having the positions 61 to 504 of the amino acid sequence set out in SEQ ID NO: 1; and ΔC represents a mutant having the positions 1 to 230 of the amino acid sequence set out in SEQ ID NO: 1. Dok-7 and its mutants include a fused FLAG tag, while MuSK includes a fused myc tag.

Figure 13:
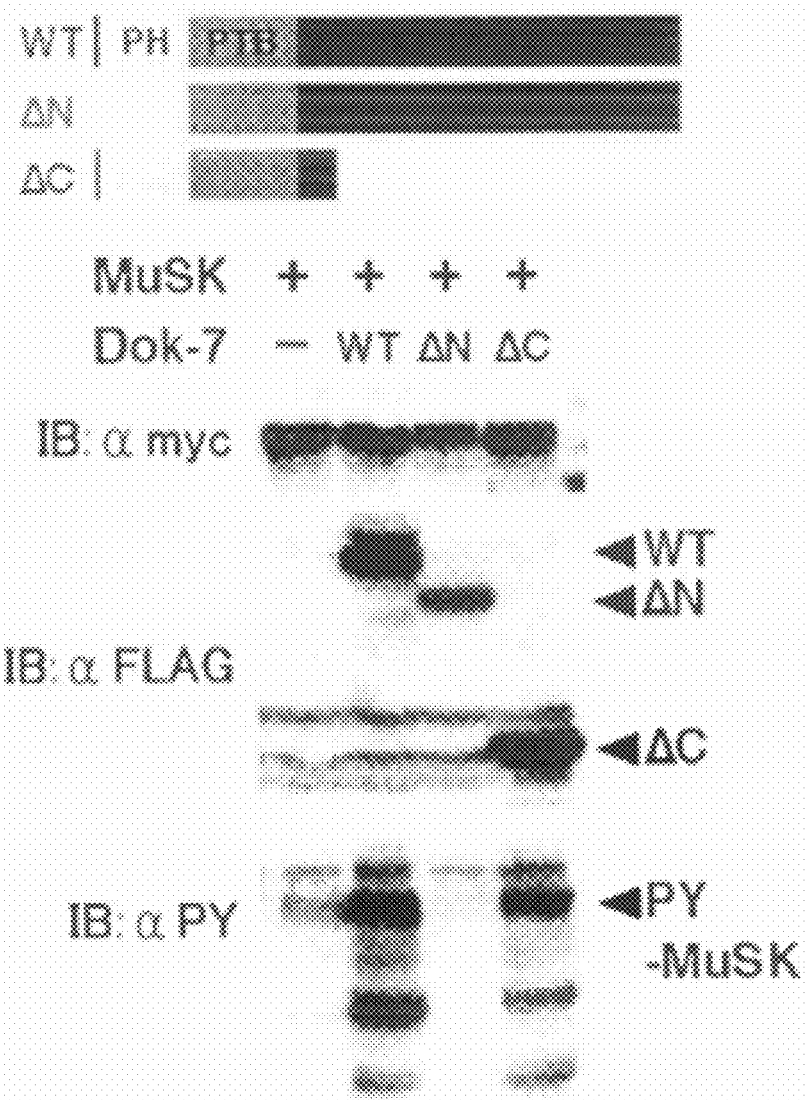
FIG. 13 illustrates the interaction of the polypeptide of the present invention with a muscle-specific tyrosine kinase.

Then, a western analysis was performed for the whole cell lysate obtained from each of the transformed cell strains. The anti-myc tag antibody (IB: αmyc), the anti-FLAG tag antibody (IB: αFLAG), and the anti-phosphorylated tyrosine antibody (IB: αPY) used in the western analysis were all the same as those in the foregoing. The results are shown in FIG. 13. The upper panel in FIG. 13 shows a schematic view of each Dok-7 structure (see, FIG. 26 in detail). Moreover, the middle panel in FIG. 13 shows combinations of the DNAs introduced into each 293T cell used in this analysis.

As shown in FIG. 13, tyrosine phosphorylation of MuSK was confirmed for the wild type human Dok-7 and ΔC, but not for ΔN deficient in the PH domain. These results suggested that the PH domain was essential for tyrosine phosphorylation of MuSK.

Next, the DNA of mutant Dok-7 (RA) having the substitutions of arginine at positions of 158, 159 and 174 of the amino acid sequence within the PTB domain of human Dok-7 (positions 109 to 204 of the amino acid sequence set out in SEQ ID NO: 1) with alanine was produced by point mutagenesis according to a common procedure. Transformant 293T cell strain which expressed each of the RA or wild type human Dok-7 (WT), and permitted forced expression of MuSK was produced according to a procedure to similar that described above. Also in this study, a myc tag was fused to MuSK.

Figure 14:
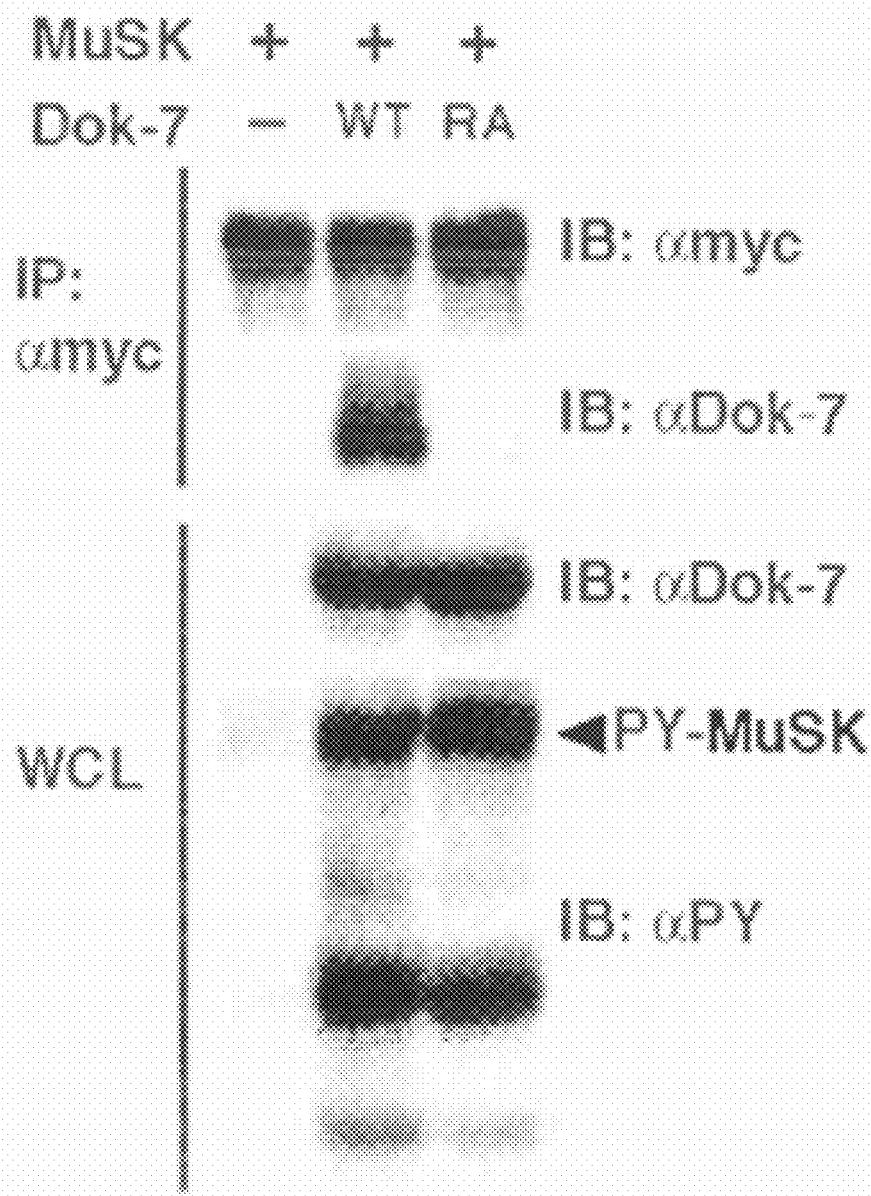
FIG. 14 illustrates the interaction of the polypeptide of the present invention with a muscle-specific tyrosine kinase.

Then, immunoprecipitation of whole cell lysate (WCL) obtained from each transformed cell strain was carried out, and a western analysis was performed on the resulting immunoprecipitate (IP: αmyc). The antibodies used were the same as the antibodies described above. The results are shown in FIG. 14. The upper panel in FIG. 14 shows combinations of the DNAs introduced into each 293T cell used in this analysis.

As shown in FIG. 14, the wild type human Dok-7 bound to and coprecipitated with MuSK, while RA having the mutation in the PTB domain was not found to bind to and coprecipitate with MuSK. From these results, it was suggested that the PTB domain involved in binding of Dok-7 to MuSK.

Meanwhile, it was suggested that the PTB domain of Dok-7 is not significant in inducing the tyrosine phosphorylation of MuSK in at least 293T cells since RA of Dok-7 promotes the tyrosine phosphorylation of MuSK.

Figure 15:
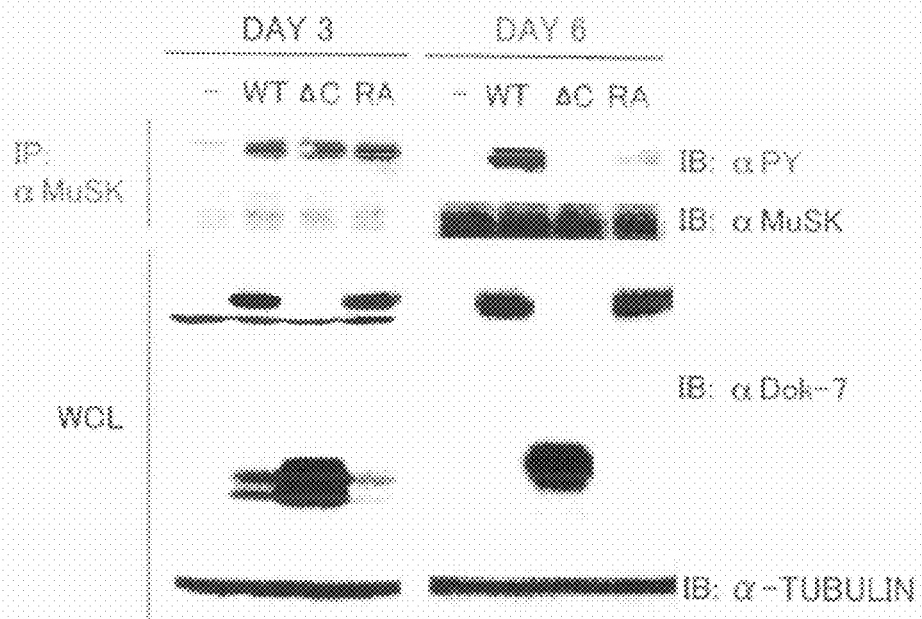
FIG. 15 illustrates the interaction of the polypeptide of the present invention with a muscle-specific tyrosine kinase.

Furthermore, similar analysis was performed on the whole cell lysate (WCL) obtained from each C2 myotube (to which Dok-7 WT, ΔC, or RA gene had been each introduced already) on day 3 and 6 following initiation of differentiation, and on the immunoprecipitate (IP: αMuSK) obtained by carrying out immunoprecipitation on this whole cell lysate. The results are shown in FIG. 15. On day 3 following initiation of the differentiation, C2 myotube was just slightly formed, and the differentiation was completed on day 6 following initiation of the differentiation.

In addition, the number of AChR clusters of each C2 myotube on day 7 following initiation of the differentiation was counted according to the procedure described above. The results are shown in FIG. 16.

As shown in FIG. 15, on day 3 and day 6 following initiation of the differentiation, the wild type Dok-7 protein could promote tyrosine phosphorylation of endogenous MuSK. In contrast, RA and ΔC could promote the tyrosine phosphorylation of endogenous MuSK on day 3 following initiation of the differentiation (in mid course of differentiation), but the tyrosine phosphorylation of endogenous MuSK was not promoted on day 6 following initiation of the differentiation (after completing the differentiation).

Figure 16:
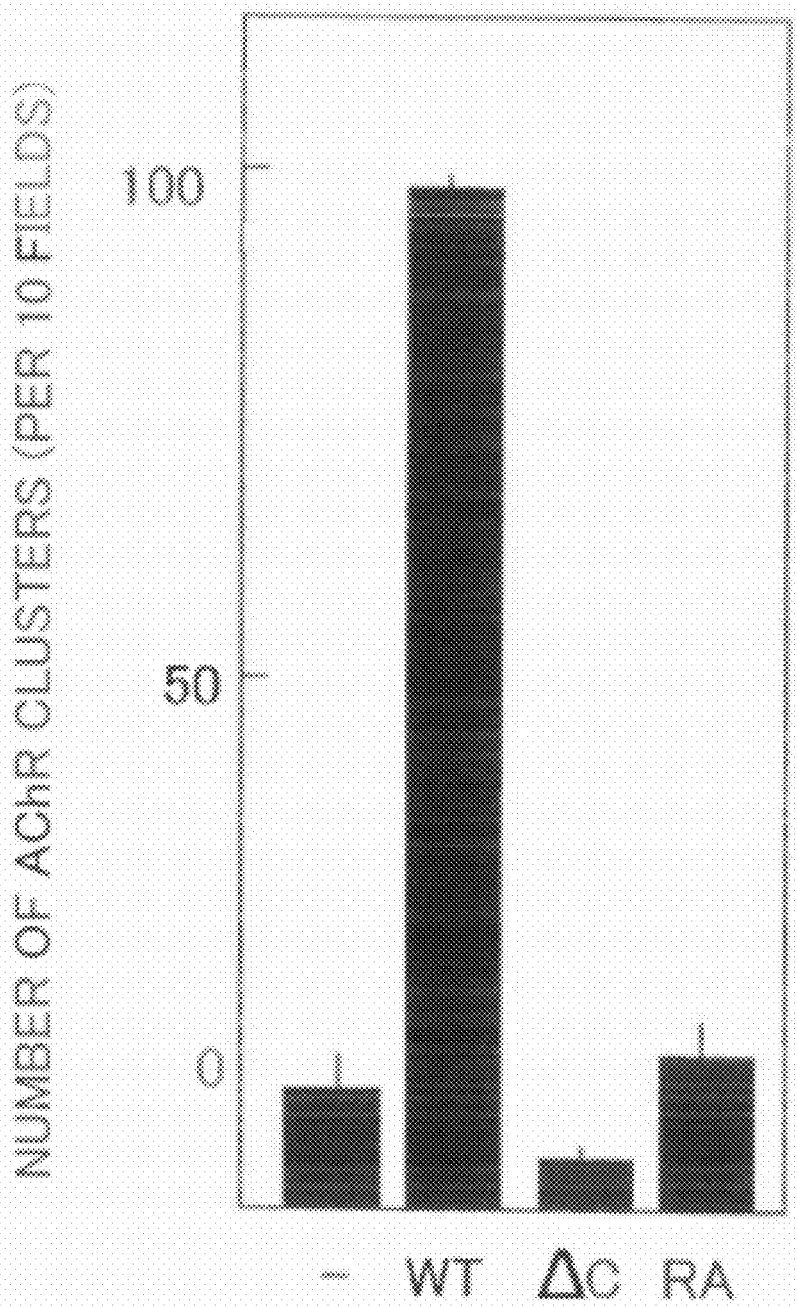
FIG. 16 illustrates the state of cluster formation of the acetylcholine receptors induced by forced expression of the DNA of the present invention.

Furthermore, as shown in FIG. 16, the wild type Dok-7 protein led to increase in the number of AChR clusters. In contrast, with respect to RA, ΔC, increase in the number of AChR clusters in C2 myotube following differentiation was hardly found.

From these results, it was suggested that the PTB domain and the C-terminal region are necessary for activation of MuSK, and clustering of AChR in the C2 myotube following differentiation. Moreover, with respect to ΔN of Dok-7 shown in FIG. 13, tyrosine phosphorylation of MuSK was not promoted also in the C2 myotube following differentiation, and the clustering of AChR was not induced (not shown in the Figure). In general, the PH domain has been known to involve in membrane localization of proteins. Therefore, it was suggested that membrane localization of Dok-7 plays an important role in tyrosine phosphorylation of MuSK.

In summary of the results in the foregoing, a mechanism of potentiation of an intracellular inhibitory factor on activation of MuSK during the process of differentiation to myotube is speculated.

Example 10

Reverse Genetic Analysis (A) Relationship with Agrin

Nucleotide sequences of siRNA (siD-7) that specifically suppresses expression of Dok-7, and siRNA (control plot) used in a control plot were as follows (both manufactured by QIAGEN GmbH).

```
                                       (SEQ ID NO: 9)
siD-7:         5'-CACCACTATGACACACCTCGA-3'
                                       (SEQ ID NO: 10)
control plot:  5'-AATTCTCCGAACGTGTCACGT-3'
```

The siRNA was introduced into C2 myogenic cells, and differentiation was allowed, whereby the transformed myotube accompanied by suppressed Dok-7 expression was produced. The method of this transformation was conducted by a similar procedure in the aforementioned method except that "X-tremeGENE siRNA reagent" (manufactured by Roche) was used in place of "Lipofectamine2000".

The western analysis was performed on each of: immunoprecipitates (IP: αMuSK, IP: αDok-7) obtained by immunoprecipitation of the untreated cell lysate or the cell lysate following a treatment with 10 ng/ml of neural agrin (Ag) for 15 min of the transformed myotube and wild type myotube, respectively; and the isolates (BP) obtained by pulling down of the same with Btx. The antibodies used were the same as the antibodies described above. For the detection with the phosphorylated tyrosine antibody, the detection time was 10 seconds, and 1 minute. The results are shown in FIG. 17.

Additionally, the number of AChR clusters was counted after a treatment with 10 ng/ml of neural agrin (Ag) for 12 hrs, or in untreated each myotube. The results are shown in FIG. 18.

Figure 19:
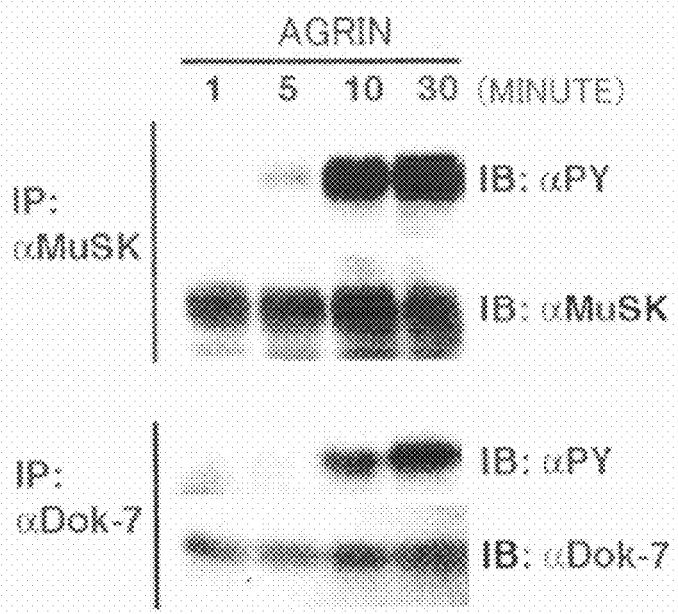
FIG. 19 illustrates time dependent alteration of phosphorylation of the polypeptide of the present invention, and a muscle-specific tyrosine kinase.

Moreover, time dependent alteration of tyrosine phosphorylation of MuSK and Dok-7 when the C2 myotube was treated with 10 ng/ml of neural agrin for 30 min (1 min, 5 min, 10 min, and 30 min after starting the treatment) was studied by performing a western analysis of immunoprecipitate (IP: αMuSK, IP: αDok-7) with each of the antibodies. The results are shown in FIG. 19.

Figure 17:
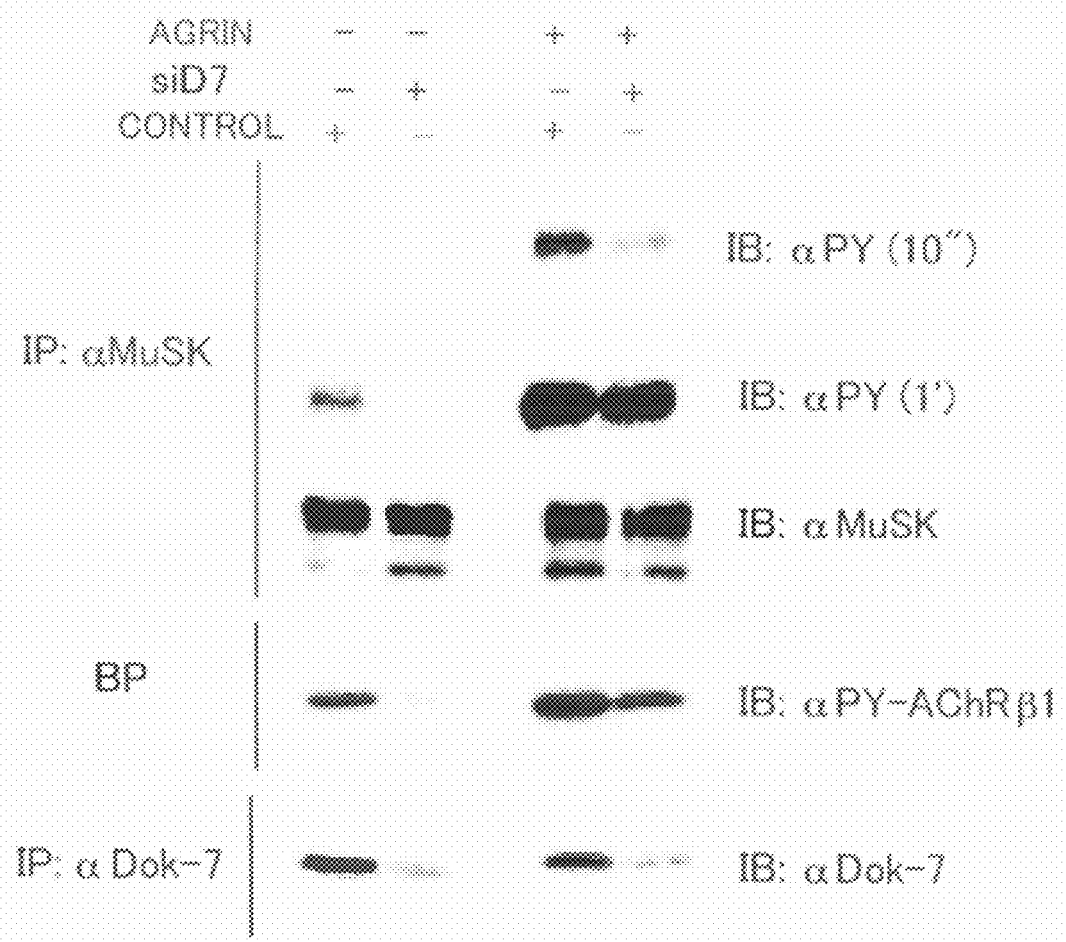
FIG. 17 illustrates the phosphorylation of a muscle-specific tyrosine kinase and a substrate thereof altered by suppressing the expression of the DNA of the present invention.

As shown in FIG. 17, when expression of endogenous Dok-7 was suppressed by siD-7, tyrosine phosphorylation of MuSK and AChRβ1 in the absence of agrin was inhibited. Similarly, MuSK activation and phosphorylation of AChRβ1 which are agrin dependent were also inhibited.

Figure 18:
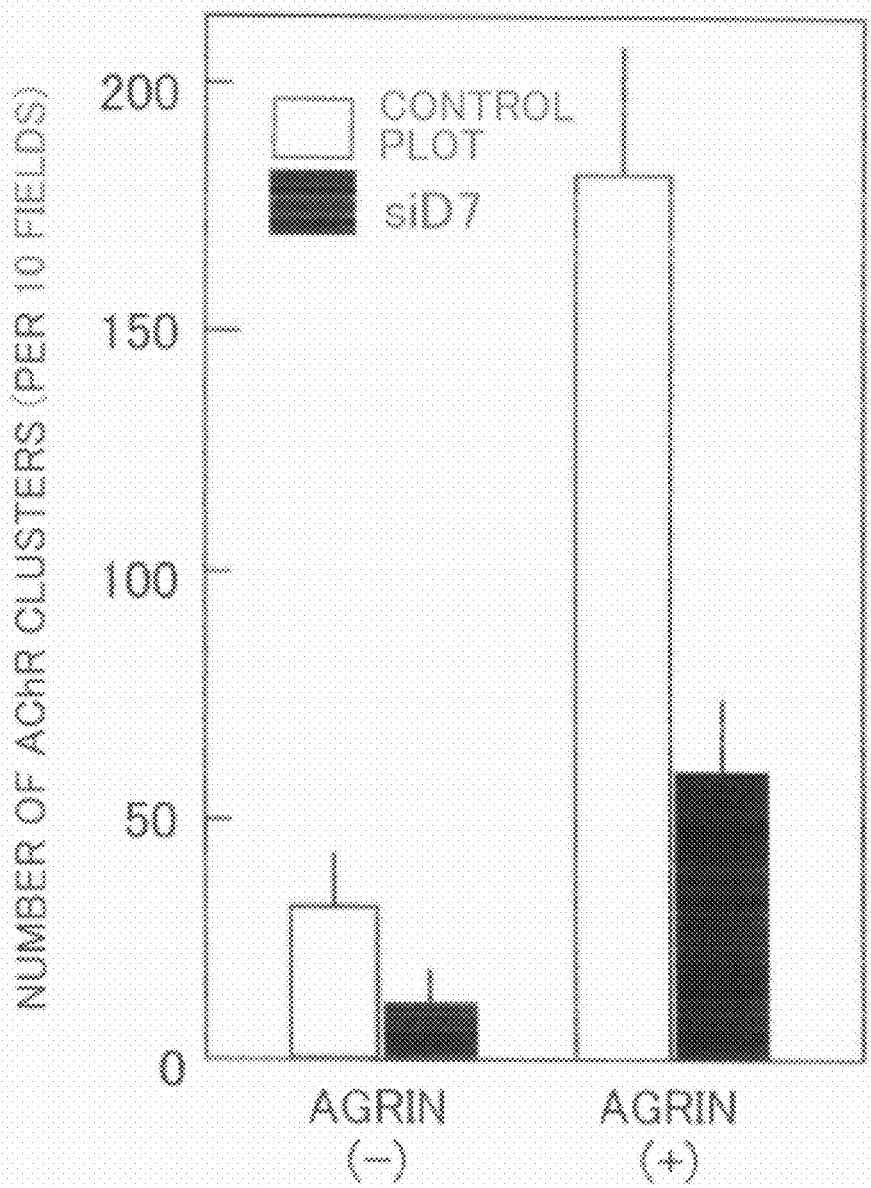
FIG. 18 illustrates the state of cluster formation of the acetylcholine receptors altered by suppressing the expression of the DNA of the present invention.

In addition, as shown in FIG. 18, when expression of endogenous Dok-7 was suppressed by siD-7, both agrin-dependent and agrin-independent clustering of AChR was prevented.

For reference, the fact that MuSK is requisite in cluster formation of AChR by agrin has been already known (see, H. Zhou, D. J. Glass, G. D. Yancopoulos, and J. R. Sanes, "Journal of Cell Biology", 146, 1133 (1999); R. Herbst, and S. J. Burden, "EMBO Journal", 19, 67 (2000)).

From these results, it was proven that Dok-7 plays an essential role in activation of MuSK, and MuSK-dependent cluster formation of AChR in myotube.

As shown in FIG. 19, similar time dependent alteration was exhibited for tyrosine phosphorylation of endogenous MuSK, and tyrosine phosphorylation of endogenous Dok-7 in C2 myotube cells stimulated with agrin. Thus, in spite of the results described above, it was suggested that the possibility cannot be excluded that Dok-7 may play a role downstream of the signal transduction pathway in which MuSK is involved.

Example 11

Reverse Genetic Analysis (Level in Individual)

(A) Production of Knock Out Mouse

Figure 20:
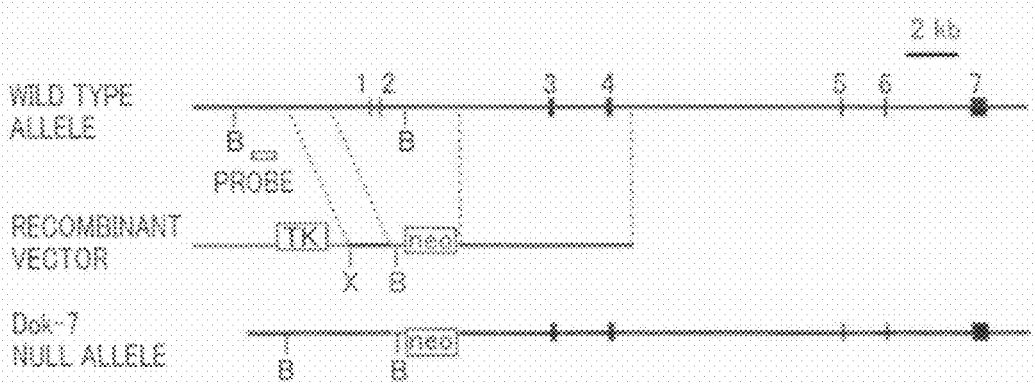
FIG. 20 illustrates a map of the gene of the present invention.

A bacterial artificial chromosome (BAC) clone including a mouse dok-7 gene locus was obtained from BACPAC Resource Center (upper column in FIG. 20). The recombinant vector was constructed with the dok-7 gene to include the substitution of the first and the second exons (each exon being represented by number of 1 to 7) with a neomycin phosphotransferase gene, such that this neomycin phosphotransferase gene DNA was positioned adjacent to a 5' fragment (1.8 kb) and a 3' fragment (7.3 kb) of the dok-7 gene DNA (FIG. 20, middle column). This construct was linearized, and electroporated into embryonic stem cells of 129/Ola origin, whereby three homologous recombinants were identified. A chimeric male was mated with a C57BL/6 female, and thus a chimera germ cell line, and a hetero conjugate in turn were obtained. In FIG. 20: B represents a BglII restriction site; X represents a XhoI restriction site; and neo represents a neomycin resistance gene.

In order to verify the insertion of the recombinant vector, the DNA was purified from the tail of each of the wild type mouse, the hetero mouse, and the null mouse. After this DNA was subjected to a restriction enzyme treatment with BglII, a Southern analysis was performed using a probe corresponding to the sequence shown in the upper column in FIG. 20 according to a common procedure. The results are shown in FIG. 21.

Figure 21:
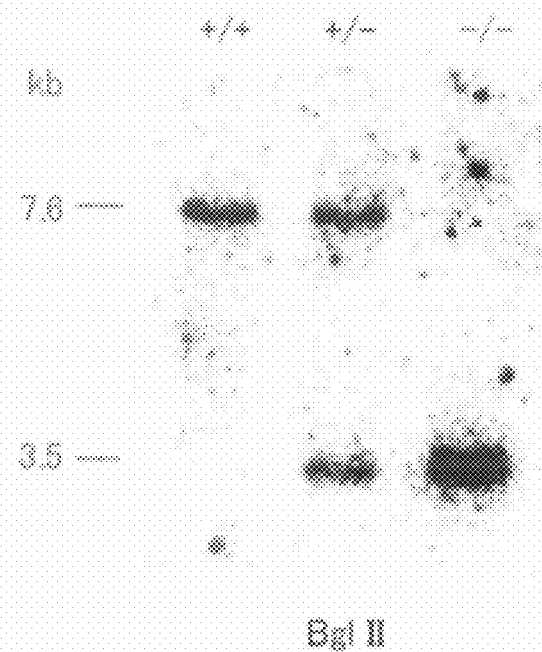
FIG. 21 illustrates the presence/absence of knock out of the DNA of the present invention.

As shown in FIG. 21, a band was detected at 7.6 kb in the wild type mouse and the hetero mouse, while this band was not detected in the null mouse. Furthermore, a band at 3.5 kb not detected in the wild type mouse was detected in the hetero mouse and the null mouse. From the results as described above, it was ascertained that homologous recombination of the exons 1 and 2 occurred with the recombinant vector in the null mouse, whereby a null allele was yielded.

In addition, the western analysis was performed using each muscular extract of the wild type mouse and the null mouse as a sample, with an anti-Dok-7 antibody which can detect a peptide that corresponds to the area of exons 6 and 7. The results are shown in FIG. 22.

Figure 22:
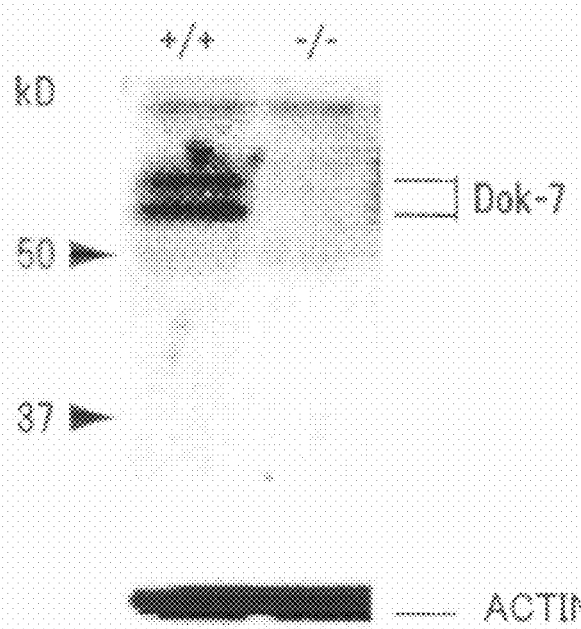
FIG. 22 illustrates the presence/absence of the polypeptide of the present invention.

As shown in FIG. 22, a band expected as Dok-7 was detected in the wild type mouse, whereas any band was not detected in the null mouse. Therefore, it was revealed that the Dok-7 protein had not been synthesized in the null mouse.

(B) Respiration

The wild type mouse and the hetero mouse which are littermates exhibited a normal state. In contrast, the Dok-7 null mouse could not move at birth, and died immediately after birth. In addition, since respiratory failure was predicted in the null mouse, the lung of the null mouse was stained with hematoxylin eosin, and thereafter observed. The results are shown in FIG. 23.

Figure 23:
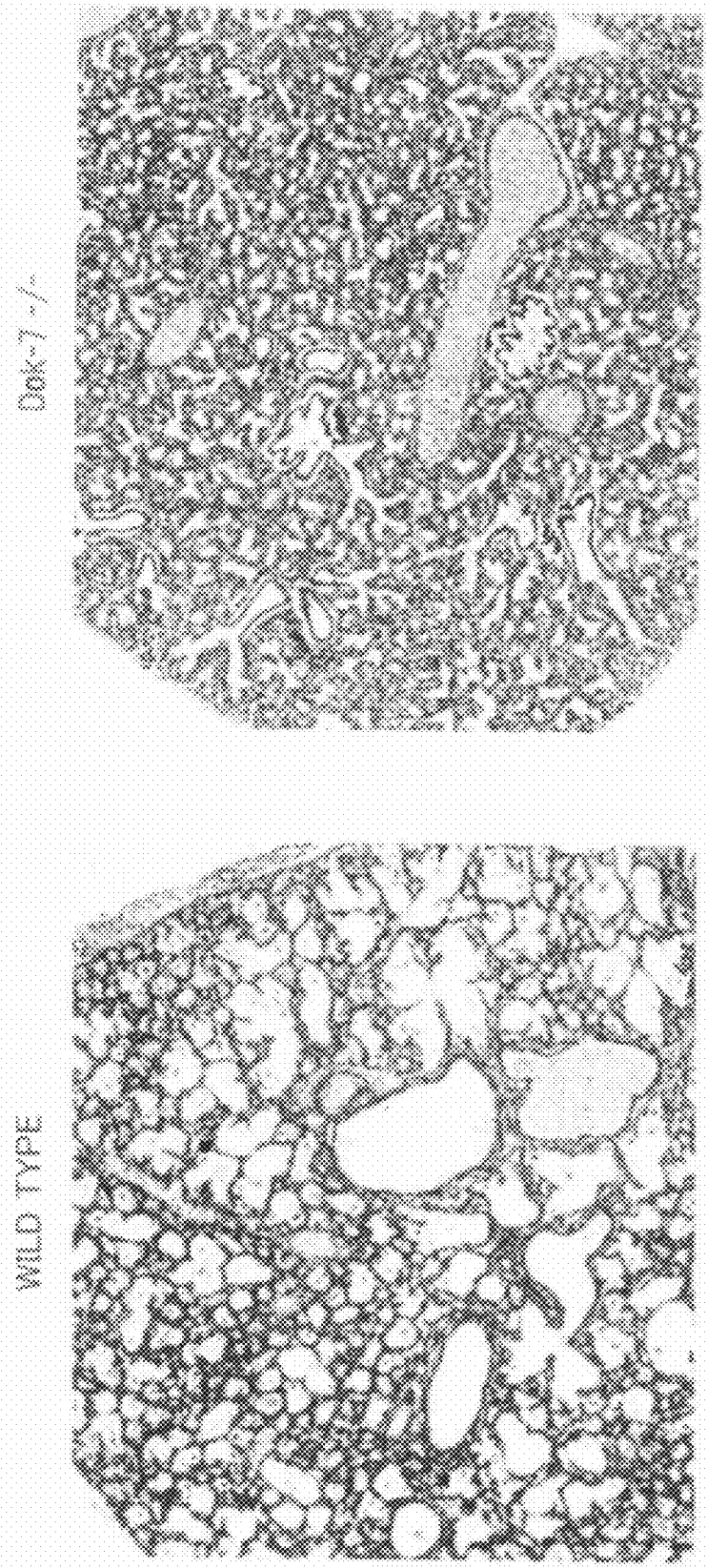
FIG. 23 illustrates the state of a lung altered by knock out of the DNA of the present invention.

As shown in FIG. 23, the air sac of the pulmonary alveolus was expanded in the wild type mouse, but not in the null mouse to the contrary. From these results, respiratory failure in the null mouse was confirmed.

(C) NMJ

Figure 24:
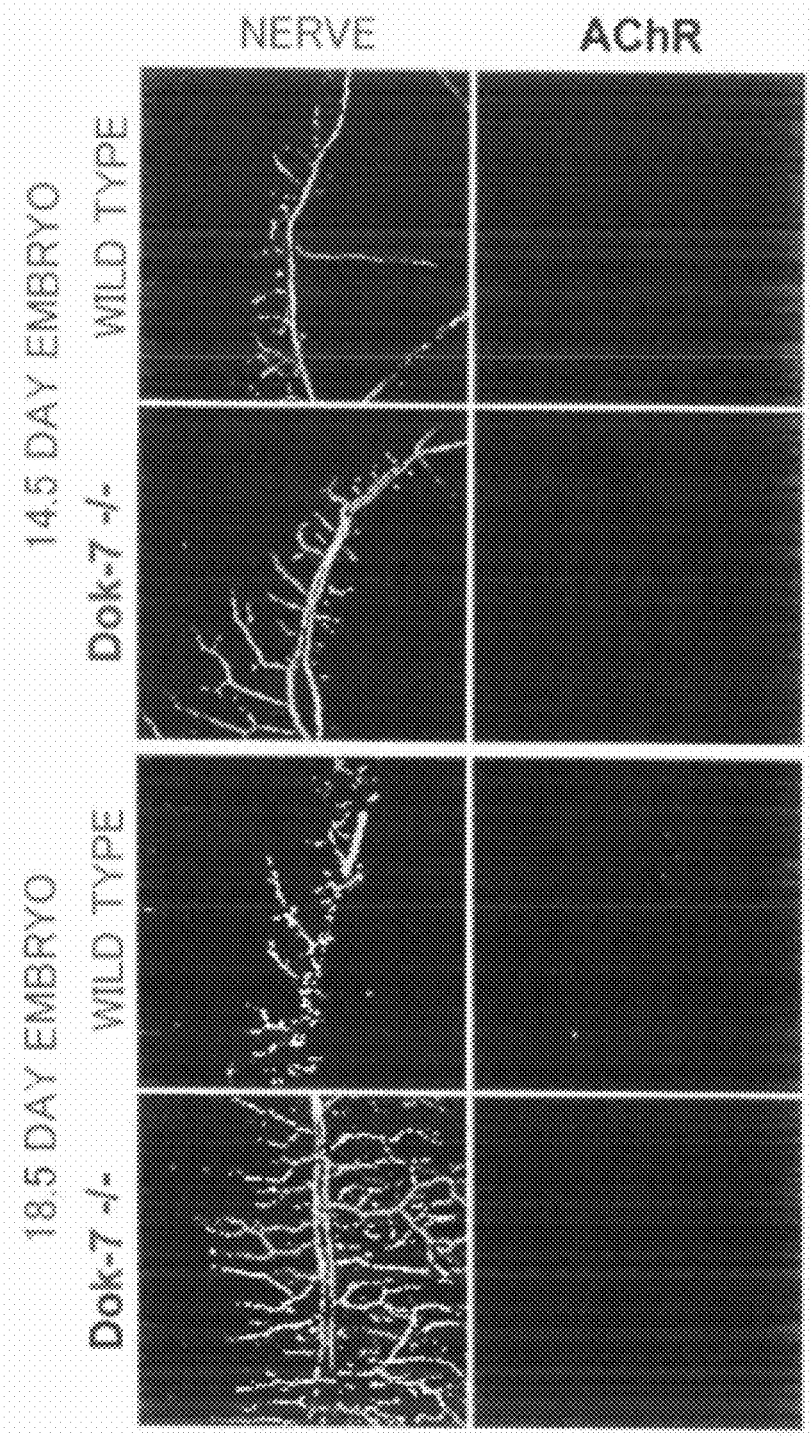
FIG. 24 illustrates the state of cluster formation of acetylcholine receptors altered by knock out of the DNA of the present invention.

The diaphragmatic muscle was prepared from each embryo (14.5 day embryo, and 18.5 day embryo) of the wild type mouse and the null mouse, and then the nerve and AChR were visualized in the diaphragmatic muscle by anti-neurofilament staining and Btx staining, respectively. The results of observation of thus visualized diaphragmatic muscle are shown in FIG. 24. The bar in FIG. 24 represents the size of 100 μm.

As shown in FIG. 24, in both 14.5 day embryo and 18.5 day embryo of the null mouse, any AChR cluster was not detected in the endplate region of the diaphragmatic muscle. Generally, nascent AChR clusters are formed in a nerve/agrin independent manner in the 14.5-day embryo, while AChR cluster formation was found in a nerve/agrin dependent manner in the 18.5 day embryo. Therefore, it was suggested that Dok-7 was required in either type of MuSK-dependent postsynaptic specialization. Furthermore, in 18.5 day embryo of the null mouse, the axon collateral that extends from the motor nerve trunk was aberrantly long in the endplate region of the diaphragm, and did not terminate in the vicinity of the nerve trunk.

Since these abnormalities could not be distinguished from abnormalities found in MuSK-deficient mouse, Dok-7 is suggested to play an essential role in vivo in MuSK-dependent biological process, i.e., neuromuscular synaptogenesis.

Example 12

Relationship between Dok-7 and Congenital Myasthenic Syndrome

Congenital myasthenic syndrome has been reported to correlate with genetic alteration that affects postsynaptic structure including AChR (see, Nonpatent Documents 1 and 2, supra). Further, point mutation of MuSK gene was reported as an example of genetic alteration that causes the congenital myasthenic syndrome (see, for example, F. Chevessier et al., Hum. Mol. Genet. 13, 3229 (2004)). According to this reported point mutation, the mutant MuSK gene includes an unexpressed allele, and MuSK-VM. Thus, investigation of interaction between Dok-7 and MuSK-VM was attempted.

MuSK-VM (myc tag labeled) and human Dok-7 were introduced into the 293T cells according to the aforementioned method to produce transformant 293T cells. Next, the western analysis was performed for the whole cell lysate (WCL) obtained from the transformant 293T cell, and the immunoprecipitate (IP: αmyc) obtained by the immunoprecipitation of this whole cell lysate. The antibodies used were the same as the antibodies described above. The results are shown in FIG. 25. The upper panel in FIG. 25 shows combinations of the DNAs introduced into each 293T cell used in this analysis.

As shown in FIG. 25, in the transformant 293T cells in which forced expression of Dok-7 was permitted, the wild type MuSK protein (WT) bound to the wild type Dok-7 protein, while the mutant MuSK protein (VM) hardly bound to the wild type Dok-7 protein.

In summary of the aforementioned results, the mechanism of congenital myasthenic syndrome as described below can be speculated. Genetic alteration in MuSK and/or Dok-7 leads to decrease in interaction between MuSK with Dok-7. As a result, symptoms of the congenital myasthenic syndrome are developed since cluster formation of AChR in the myotube is inhibited.

INDUSTRIAL APPLICABILITY

Administration of the polypeptide and/or DNA of the present invention to a patient suffering from congenital myasthenic syndrome due to mutation in Dok-7 gene DNA accelerates cluster formation of AChR via tyrosine phosphorylation of MuSK, and phosphorylation of AChRβ1. Consequently, the congenital myasthenic syndrome can be treated or prevented. In addition, determination of the nucleotide sequence of the DNA of the present invention enables congenital myasthenic syndrome to be examined.

The invention claimed is:

1. An isolated DNA encoding a polypeptide consisting of the amino acid sequence set out in SEQ ID NO: 1.

2. An isolated DNA comprising: a nucleotide sequence having at least 95% identity to SEQ ID NO. 2, encoding a polypeptide that activates a muscle-specific tyrosine kinase (MuSK), wherein the polypeptide comprises an amino acid sequence consisting of the amino acids of positions 8 to 107, an amino acid sequence consisting of the amino acids of positions 109 to 204, and an amino acid sequence consisting of the amino acids of positions 231 to 504 set out in SEQ ID NO: 1 in the above-described order, and has activity of promoting tyrosine-phosphorylation in MuSK and of accelerating clustering of acetylcholine receptors.

3. A method for preparing a vector encoding a polypeptide that activates a muscle-specific tyrosine kinase comprising inserting the DNA according to claim 1 or 2 into a vector.

4. An isolated cell in which a vector encoding a polypeptide that activates a muscle-specific tyrosine kinase comprising the DNA according to claim 1 or 2 is introduced.

* * * * *

SEQUENCE LISTING

```
<160> NUMBER OF SEQ ID NOS: 10

<210> SEQ ID NO 1
<211> LENGTH: 504
<212> TYPE: PRT
<213> ORGANISM: Artificial Sequence
<220> FEATURE:
<223> OTHER INFORMATION: Homo sapiens

<400> SEQUENCE: 1

Met Thr Glu Ala Ala Leu Val Glu Gly Gln Val Lys Leu Arg Asp Gly
1               5                   10                  15

Lys Lys Trp Lys Ser Arg Trp Leu Val Leu Arg Lys Pro Ser Pro Val
            20                  25                  30

Ala Asp Cys Leu Leu Met Leu Val Tyr Lys Asp Lys Ser Glu Arg Ile
        35                  40                  45

Lys Gly Leu Arg Glu Arg Ser Ser Leu Thr Leu Glu Asp Ile Cys Gly
    50                  55                  60

Leu Glu Pro Gly Leu Pro Tyr Glu Gly Leu Val His Thr Leu Ala Ile
65                  70                  75                  80

Val Cys Leu Ser Gln Ala Ile Met Leu Gly Phe Asp Ser His Glu Ala
                85                  90                  95

Met Cys Ala Trp Asp Ala Arg Ile Arg Tyr Ala Leu Gly Glu Val His
            100                 105                 110

Arg Phe His Val Thr Val Ala Pro Gly Thr Lys Leu Glu Ser Gly Pro
        115                 120                 125

Ala Thr Leu His Leu Cys Asn Asp Val Leu Val Leu Ala Arg Asp Ile
    130                 135                 140

Pro Pro Ala Val Thr Gly Gln Trp Lys Leu Ser Asp Leu Arg Arg Tyr
145                 150                 155                 160

Gly Ala Val Pro Ser Gly Phe Ile Phe Glu Gly Gly Thr Arg Cys Gly
                165                 170                 175

Tyr Trp Ala Gly Val Phe Phe Leu Ser Ser Ala Glu Gly Glu Gln Ile
            180                 185                 190

Ser Phe Leu Phe Asp Cys Ile Val Arg Gly Ile Ser Pro Thr Lys Gly
        195                 200                 205

Pro Phe Gly Leu Arg Pro Val Leu Pro Asp Pro Ser Pro Pro Gly Pro
    210                 215                 220

Ser Thr Val Glu Glu Arg Val Ala Gln Glu Ala Leu Glu Thr Leu Gln
225                 230                 235                 240
```

Leu Glu Lys Arg Leu Ser Leu Leu Ser His Ala Gly Arg Pro Gly Ser
                245                 250                 255

Gly Gly Asp Asp Arg Ser Leu Ser Ser Ser Ser Glu Ala Ser His
            260                 265                 270

Leu Asp Val Ser Ala Ser Ser Arg Leu Thr Ala Trp Pro Glu Gln Ser
                275                 280                 285

Ser Ser Ala Ser Thr Ser Gln Glu Gly Pro Arg Pro Ala Ala Ala
    290                 295                 300

Gln Ala Ala Gly Glu Ala Met Val Gly Ala Ser Arg Pro Pro Lys
305                 310                 315                 320

Pro Leu Arg Pro Arg Gln Leu Gln Glu Val Gly Arg Gln Ser Ser Ser
                325                 330                 335

Asp Ser Gly Ile Ala Thr Gly Ser His Ser Ser Tyr Ser Ser Leu
                340                 345                 350

Ser Ser Tyr Ala Gly Ser Ser Leu Asp Val Trp Arg Ala Thr Asp Glu
                355                 360                 365

Leu Gly Ser Leu Leu Ser Leu Pro Ala Ala Gly Ala Pro Glu Pro Ser
                370                 375                 380

Leu Cys Thr Cys Leu Pro Gly Thr Val Glu Tyr Gln Val Pro Thr Ser
385                 390                 395                 400

Leu Arg Ala His Tyr Asp Thr Pro Arg Ser Leu Cys Leu Ala Pro Arg
                405                 410                 415

Asp His Ser Pro Pro Ser Gln Gly Ser Pro Gly Asn Ser Ala Ala Arg
                420                 425                 430

Asp Ser Gly Gly Gln Thr Ser Ala Gly Cys Pro Ser Gly Trp Leu Gly
                435                 440                 445

Thr Arg Arg Arg Gly Leu Val Met Glu Ala Pro Gln Gly Ser Glu Ala
                450                 455                 460

Thr Leu Pro Gly Pro Ala Pro Gly Glu Pro Trp Glu Ala Gly Pro
465                 470                 475                 480

His Ala Gly Pro Pro Pro Ala Phe Phe Ser Ala Cys Pro Val Cys Gly
                485                 490                 495

Gly Leu Lys Val Asn Pro Pro Pro
            500

<210> SEQ ID NO 2
<211> LENGTH: 1515
<212> TYPE: DNA
<213> ORGANISM: Artificial Sequence
<220> FEATURE:
<223> OTHER INFORMATION: Homo Sapiens

<400> SEQUENCE: 2
atgaccgagg cggcgctggt ggagggccag gtcaagctgc ggacggcaa gaagtggaag      60 agtaggtggc tggtgctgcg gaagccgtcg cccgtggcag actgcctgct gatgctggtc     120
tacaaggaca gtcggagcg tatcaagggc ctgcgggagc gcagcagcct gacgctagag     180
gacatctgcg gctggagcc cggcctgccc tacgagggct tggtccacac gctggccatt     240
gtctgcctgt cccaggccat catgctgggc tttgacagcc acgaggccat gtgtgcgtgg     300
gatgcccgga tccgctatgc gctcggcgag gtgcataggt tccatgtgac agtggctcca     360
ggcaccaagt tggagagcgg cccggctacc ctgcacctct gcaatgatgt cctcgtcttg     420 gccaggggaca tccccccggc tgtcacgggg cagtggaagc tgtctgacct ccggcgctac    480
ggggccgtgc caagcggatt catctttgaa ggcgggacca ggtgtgggta ctgggctggc     540

-continued

```
gtcttcttcc tgtcctcggc cgaggggag cagatcagct tcctgttcga ctgcatcgtc      600
cgaggcatct ccccaccaa gggccccttt gggctgcggc cggttctacc agacccaagt      660
cccccgggac cctcgactgt ggaggagcgt gtggcccagg aagccctgga accctacag      720 ctggagaagc ggctgagcct cctctcacat gcgggcaggc cgggcagtgg agggatgac      780 cgcagcctgt ccagctcatc ctcagaggcc agtcacttgg acgtcagcgc cagcagccgg      840
ctcaccgcat ggccagagca atcctcgtcg tcagccagca cgtcacagga ggggcctaga      900
ccagcagctg cccaggccgc cggggaagcc atggtgggtg cctcaaggcc accccccaag      960
ccgctgcgtc cgcggcagct gcaggaggtt ggccgccaga gctcctcgga cagcggcatc     1020
gccactggca gccactcctc ttactccagc agcctctcgt cctacgcggg cagcagcctg     1080
gacgtgtggc gggccacaga tgaactgggc tcactgctca gcctgccagc agcggggcc      1140 cccgagccca gctgtgcac ctgcctgccc gggacagtcg agtaccaggt gcccacctcc      1200
ctgcgggccc actatgacac accacgcagc ctttgcctgg ctcctagaga ccacagcccc     1260
ccctcacagg gcagccccgg caacagtgcg gccagggact caggcggcca gacgtccgcc     1320
gggtgtccct ctggctggct gggcacgaga cggcggggcc tggtgatgga ggcccccag      1380 ggcagcgagg ccacactgcc tggccctgcc cctggcgagc cctgggaagc aggcggcccc     1440
cacgcggggc cacccccggc tttcttttcg gcatgtccag tctgtggagg actcaaggta     1500
aacccccctc cttga                                                     1515
```

<210> SEQ ID NO 3
<211> LENGTH: 840
<212> TYPE: PRT
<213> ORGANISM: Artificial Sequence
<220> FEATURE:
<223> OTHER INFORMATION: Mus musculus

<400> SEQUENCE: 3

```
Met Arg Glu Leu Val Asn Ile Pro Leu Leu Gln Met Leu Thr Leu Val
1               5                   10                  15

Ala Phe Ser Gly Thr Glu Lys Leu Pro Lys Ala Pro Val Ile Thr Thr
            20                  25                  30

Pro Leu Glu Thr Val Asp Ala Leu Val Glu Glu Val Ala Thr Phe Met
        35                  40                  45

Cys Ala Val Glu Ser Tyr Pro Gln Pro Glu Ile Ser Trp Thr Arg Asn
    50                  55                  60

Lys Ile Leu Ile Lys Leu Phe Asp Thr Arg Tyr Ser Ile Arg Glu Asn
65                  70                  75                  80

Gly Gln Leu Leu Thr Ile Leu Ser Val Glu Asp Ser Asp Gly Ile
                85                  90                  95

Tyr Cys Cys Ile Ala Asn Asn Gly Val Gly Gly Ala Val Glu Ser Cys
            100                 105                 110

Gly Ala Leu Gln Val Lys Met Lys Pro Lys Ile Thr Arg Pro Pro Ile
        115                 120                 125

Asn Val Lys Ile Ile Glu Gly Leu Lys Ala Val Leu Pro Cys Thr Thr
    130                 135                 140

Met Gly Asn Pro Lys Pro Ser Val Ser Trp Ile Lys Gly Asp Asn Ala
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190
```

-continued

```
Lys Asn Ser Leu Gly Thr Ala Tyr Ser Lys Leu Val Lys Leu Glu Val
            195                 200                 205

Glu Val Phe Ala Arg Ile Leu Arg Ala Pro Glu Ser His Asn Val Thr
210                 215                 220

Phe Gly Ser Phe Val Thr Leu Arg Cys Thr Ala Ile Gly Ile Pro Val
225                 230                 235                 240

Pro Thr Ile Ser Trp Ile Glu Asn Gly Asn Ala Val Ser Ser Gly Ser
            245                 250                 255

Ile Gln Glu Ser Val Lys Asp Arg Val Ile Asp Ser Arg Leu Gln Leu
            260                 265                 270

Phe Ile Thr Lys Pro Gly Leu Tyr Thr Cys Ile Ala Thr Asn Lys His
            275                 280                 285

Gly Glu Lys Phe Ser Thr Ala Lys Ala Ala Thr Val Ser Ile Ala
290                 295                 300

Glu Trp Ser Lys Ser Gln Lys Asp Ser Gln Gly Tyr Cys Ala Gln Tyr
305                 310                 315                 320

Arg Gly Glu Val Cys Asp Ala Val Leu Ala Lys Asp Ala Leu Val Phe
                325                 330                 335

Phe Asn Thr Ser Tyr Arg Asp Pro Glu Asp Ala Gln Glu Leu Leu Ile
            340                 345                 350

His Thr Ala Trp Asn Glu Leu Lys Ala Val Ser Pro Leu Cys Arg Pro
            355                 360                 365

Ala Ala Glu Ala Leu Leu Cys Asn His Leu Phe Gln Glu Cys Ser Pro
370                 375                 380

Gly Val Val Pro Thr Pro Met Pro Ile Cys Arg Glu Tyr Cys Leu Ala
385                 390                 395                 400

Val Lys Glu Leu Phe Cys Ala Lys Glu Trp Gln Ala Met Glu Gly Lys
                405                 410                 415

Ala His Arg Gly Leu Tyr Arg Ser Gly Met His Leu Leu Pro Val Pro
                420                 425                 430

Glu Cys Ser Lys Leu Pro Ser Met His Arg Asp Pro Thr Ala Cys Thr
            435                 440                 445

Arg Leu Pro Tyr Leu Asp Tyr Lys Lys Glu Asn Ile Thr Thr Phe Pro
450                 455                 460

Ser Ile Thr Ser Ser Arg Pro Ser Ala Asp Ile Pro Asn Leu Pro Ala
465                 470                 475                 480

Ser Thr Ser Ser Phe Ala Val Ser Pro Ala Tyr Ser Met Thr Val Ile
            485                 490                 495

Ile Ser Ile Val Ser Ser Phe Ala Leu Phe Ala Leu Leu Thr Ile Ala
            500                 505                 510

Thr Leu Tyr Cys Cys Arg Arg Arg Lys Glu Trp Lys Asn Lys Lys Arg
            515                 520                 525

Glu Ser Thr Ala Val Thr Leu Thr Thr Leu Pro Ser Glu Leu Leu Leu
530                 535                 540

Asp Arg Leu His Pro Asn Pro Met Tyr Gln Arg Met Pro Leu Leu Leu
545                 550                 555                 560

Asn Pro Lys Leu Leu Ser Leu Glu Tyr Pro Arg Asn Asn Ile Glu Tyr
            565                 570                 575

Val Arg Asp Ile Gly Glu Gly Ala Phe Gly Arg Val Phe Gln Ala Arg
            580                 585                 590

Ala Pro Gly Leu Leu Pro Tyr Glu Pro Phe Thr Met Val Ala Val Lys
            595                 600                 605

Met Leu Lys Glu Glu Ala Ser Ala Asp Met Gln Ala Asp Phe Gln Arg
610                 615                 620
```

Glu Ala Ala Leu Met Ala Glu Phe Asp Asn Pro Asn Ile Val Lys Leu
625                 630                 635                 640

Leu Gly Val Cys Ala Val Gly Lys Pro Met Cys Leu Leu Phe Glu Tyr
            645                 650                 655

Met Ala Tyr Gly Asp Leu Asn Glu Phe Leu Arg Ser Met Ser Pro His
                660                 665                 670

Thr Val Cys Ser Leu Ser His Ser Asp Leu Ser Thr Arg Ala Arg Val
            675                 680                 685

Ser Ser Pro Gly Pro Pro Leu Ser Cys Ala Glu Gln Leu Cys Ile
690                 695                 700

Ala Arg Gln Val Ala Ala Gly Met Ala Tyr Leu Ser Glu Arg Lys Phe
705                 710                 715                 720

Val His Arg Asp Leu Ala Thr Arg Asn Cys Leu Val Gly Glu Thr Met
                725                 730                 735

Val Val Lys Ile Ala Asp Phe Gly Leu Ser Arg Asn Ile Tyr Ser Ala
            740                 745                 750

Asp Tyr Tyr Lys Ala Asp Gly Asn Asp Ala Ile Pro Ile Arg Trp Met
            755                 760                 765

Pro Pro Glu Ser Ile Phe Tyr Asn Arg Tyr Thr Thr Glu Ser Asp Val
770                 775                 780

Trp Ala Tyr Gly Val Val Leu Trp Glu Ile Phe Ser Tyr Gly Leu Gln
785                 790                 795                 800

Pro Tyr Tyr Gly Met Ala His Glu Glu Val Ile Tyr Tyr Val Arg Asp
                805                 810                 815

Gly Asn Ile Leu Ala Cys Pro Glu Asn Cys Pro Leu Glu Leu Tyr Asn
            820                 825                 830

Leu Met Arg Leu Cys Trp Ser Lys
            835                 840

<210> SEQ ID NO 4
<211> LENGTH: 240
<212> TYPE: PRT
<213> ORGANISM: Artificial Sequence
<220> FEATURE:
<223> OTHER INFORMATION: Human

<400> SEQUENCE: 4

Met Thr Glu Ala Ala Leu Val Glu Gly Gln Val Lys Leu Arg Asp Gly
1               5                   10                  15

Lys Lys Trp Lys Ser Arg Trp Leu Val Leu Arg Lys Pro Ser Pro Val
            20                  25                  30

Ala Asp Cys Leu Leu Met Leu Val Tyr Lys Asp Lys Ser Glu Arg Ile
        35                  40                  45

Lys Gly Leu Arg Glu Arg Ser Ser Leu Thr Leu Glu Asp Ile Cys Gly
    50                  55                  60

Leu Glu Pro Gly Leu Pro Tyr Glu Gly Leu Val His Thr Leu Ala Ile
65                  70                  75                  80

Val Cys Leu Ser Gln Ala Ile Met Leu Gly Phe Asp Ser His Glu Ala
                85                  90                  95

Met Cys Ala Trp Asp Ala Arg Ile Arg Tyr Ala Leu Gly Glu Val His
            100                 105                 110

Arg Phe His Val Thr Val Ala Pro Gly Thr Lys Leu Glu Ser Gly Pro
        115                 120                 125

Ala Thr Leu His Leu Cys Asn Asp Val Leu Val Leu Ala Arg Asp Ile
    130                 135                 140

```
Pro Pro Ala Val Thr Gly Gln Trp Lys Leu Ser Asp Leu Arg Arg Tyr
145                 150                 155                 160

Gly Ala Val Pro Ser Gly Phe Ile Phe Glu Gly Gly Thr Arg Cys Gly
                165                 170                 175

Tyr Trp Ala Gly Val Phe Phe Leu Ser Ser Ala Glu Gly Glu Gln Ile
            180                 185                 190

Ser Phe Leu Phe Asp Cys Ile Val Arg Gly Ile Ser Pro Thr Lys Gly
        195                 200                 205

Pro Phe Gly Leu Arg Pro Val Leu Pro Asp Pro Ser Pro Pro Gly Pro
    210                 215                 220

Ser Thr Val Glu Glu Arg Val Ala Gln Glu Ala Leu Glu Thr Leu Gln
225                 230                 235                 240

<210> SEQ ID NO 5
<211> LENGTH: 240
<212> TYPE: PRT
<213> ORGANISM: Artificial Sequence
<220> FEATURE:
<223> OTHER INFORMATION: Mouse

<400> SEQUENCE: 5

Met Thr Glu Ala Ala Leu Val Glu Gly Gln Val Lys Leu Arg Asp Gly
1               5                   10                  15

Lys Lys Trp Lys Ser Arg Trp Leu Val Leu Arg Lys Pro Ser Pro Val
            20                  25                  30

Ala Asp Cys Leu Leu Met Leu Val Tyr Lys Asp Lys Cys Glu Arg Ser
            35                  40                  45

Lys Gly Leu Arg Glu Arg Ser Ser Leu Thr Leu Glu Asp Ile Cys Gly
    50                  55                  60

Leu Glu Pro Ala Leu Pro Tyr Glu Gly Leu Ala His Thr Leu Ala Ile
65                  70                  75                  80

Ile Cys Leu Ser Gln Ala Val Met Leu Gly Phe Asp Ser His Glu Ala
                85                  90                  95

Met Cys Ala Trp Asp Thr Arg Ile Arg Tyr Ala Leu Gly Glu Val His
            100                 105                 110

Arg Phe His Val Thr Val Ala Pro Gly Thr Lys Leu Glu Ser Gly Pro
        115                 120                 125

Ala Thr Leu His Leu Cys Asn Asp Ile Leu Val Leu Ala Arg Asp Ile
    130                 135                 140

Pro Pro Thr Val Met Gly Gln Trp Lys Leu Ser Asp Leu Arg Arg Tyr
145                 150                 155                 160

Gly Ala Val Pro Asn Gly Phe Ile Phe Glu Gly Gly Thr Arg Cys Gly
                165                 170                 175

Tyr Trp Ala Gly Val Phe Phe Leu Ser Ser Ala Glu Gly Glu Gln Met
            180                 185                 190

Ser Phe Leu Phe Asp Cys Ile Val Arg Gly Ile Ser Pro Thr Lys Gly
        195                 200                 205

Pro Phe Gly Leu Arg Pro Val Leu Pro Asp Pro Ser Ser Gly Gly Pro
    210                 215                 220

Ser Ala Ser Glu Glu Arg Val Ala Gln Glu Ala Leu Glu Ala Leu Gln
225                 230                 235                 240

<210> SEQ ID NO 6
<211> LENGTH: 236
<212> TYPE: PRT
<213> ORGANISM: Artificial Sequence
<220> FEATURE:
<223> OTHER INFORMATION: FUGU RUBRIPE
```

<400> SEQUENCE: 6

| Met | Thr | Asp | Ser | Val | Val | Glu | Gly | Tyr | Ala | Arg | Leu | Arg | Asp | Gly |
| 1   |     |     |     | 5   |     |     |     |     | 10  |     |     |     |     | 15  |

| Lys | Lys | Trp | Lys | Thr | Arg | Trp | Leu | Val | Leu | Arg | Lys | Pro | Ser | Pro | Val |
|     |     |     | 20  |     |     |     |     | 25  |     |     |     |     | 30  |     |     |

| Ala | Asp | Cys | Leu | Leu | Leu | Leu | Val | Phe | Lys | Asp | Lys | Ser | Asp | Lys | Val |
|     |     |     | 35  |     |     |     |     | 40  |     |     |     |     | 45  |     |     |

| Gln | Gly | Asn | Lys | Glu | Arg | Leu | Ser | Ala | Thr | Leu | Glu | Glu | Leu | Cys | Gly |
|     |     | 50  |     |     |     |     | 55  |     |     |     |     | 60  |     |     |     |

| Leu | Glu | Val | Gly | Pro | Trp | Tyr | Glu | Gly | Val | Ala | Phe | Thr | Leu | Ala | Ile |
| 65  |     |     |     |     | 70  |     |     |     |     | 75  |     |     |     |     | 80  |

| Leu | Cys | Leu | Thr | Gln | Thr | Thr | Leu | Leu | Gly | Phe | Asp | Ser | Lys | Glu | Ala |
|     |     |     |     | 85  |     |     |     |     | 90  |     |     |     |     | 95  |     |

| Leu | Leu | Ala | Trp | Asp | Ala | Arg | Leu | Arg | Tyr | Ser | Leu | Gly | Glu | Val | His |
|     |     |     |     | 100 |     |     |     |     | 105 |     |     |     |     | 110 |     |

| Arg | Phe | Ser | Val | Gly | Val | Leu | Pro | Gly | Thr | Lys | Leu | Glu | Ser | Gly | Pro |
|     |     |     | 115 |     |     |     |     | 120 |     |     |     |     | 125 |     |     |

| Ala | Thr | Leu | His | Leu | Cys | Asn | Asn | Leu | Leu | Ala | Leu | Ala | Arg | Asp | Val |
|     | 130 |     |     |     |     | 135 |     |     |     |     | 140 |     |     |     |     |

| Pro | Pro | Val | Ile | Val | Gly | His | Trp | Asn | Leu | Pro | Asp | Leu | Arg | Arg | Tyr |
| 145 |     |     |     |     | 150 |     |     |     |     | 155 |     |     |     |     | 160 |

| Gly | Pro | Val | Pro | Asn | Gly | Phe | Val | Phe | Glu | Gly | Gly | Thr | Arg | Cys | Gly |
|     |     |     |     | 165 |     |     |     |     | 170 |     |     |     |     | 175 |     |

| Tyr | Trp | Ala | Gly | Val | Phe | Leu | Leu | Ala | Ser | Val | Glu | Ser | Glu | Gln | Ile |
|     |     |     | 180 |     |     |     |     | 185 |     |     |     |     | 190 |     |     |

| Ser | Phe | Leu | Phe | Asp | Cys | Ile | Val | Arg | Gly | Ile | Ser | Pro | Thr | Arg | Gly |
|     |     | 195 |     |     |     |     | 200 |     |     |     |     | 205 |     |     |     |

| Pro | Phe | Gly | Leu | Arg | Pro | Val | Leu | Pro | Asp | Pro | Ser | Thr | Ser | Glu | Thr |
|     |     | 210 |     |     |     |     | 215 |     |     |     |     | 220 |     |     |     |

| Ser | Ser | Glu | Glu | Arg | Leu | Asn | His | Glu | Thr | Leu | Glu |
| 225 |     |     |     |     | 230 |     |     |     |     | 235 |     |

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
atgaccgagg cggcgctggt gg                                        22

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8
tcaaggaggg ggggtttacc ttg                                       23

<210> SEQ ID NO 9
<211> LENGTH: 21
<212> TYPE: DNA
<213> ORGANISM: Artificial Sequence
<220> FEATURE:
<223> OTHER INFORMATION: Synthetic

```
<400> SEQUENCE: 9
caccactatg acacacctcg a                                          21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
aattctccga acgtgtcacg t                                          21
```